United States Patent
Trieu

(10) Patent No.: US 9,989,543 B2
(45) Date of Patent: Jun. 5, 2018

(54) COMPOSITION, DEVICE, AND METHOD FOR DETECTING OLMESARTAN AND IMPROVING COMPLIANCE IN TREATING HYPERTENSION

(71) Applicant: Autotelic LLC, City of Industry, CA (US)

(72) Inventor: Vuong Trieu, Agoura Hills, CA (US)

(73) Assignee: AUTOTELIC, LLC, City of Industry, CA (US)

(*) Notice: Subject to any disclaimer, the term of this patent is extended or adjusted under 35 U.S.C. 154(b) by 0 days. days.

(21) Appl. No.: 15/402,990

(22) Filed: Jan. 10, 2017

(65) Prior Publication Data

US 2017/0199208 A1 Jul. 13, 2017

Related U.S. Application Data

(60) Provisional application No. 62/277,406, filed on Jan. 11, 2016.

(51) Int. Cl.
*G01N 33/558* (2006.01)
*C07K 16/44* (2006.01)
*G01N 33/94* (2006.01)

(52) U.S. Cl.
CPC ......... *G01N 33/9453* (2013.01); *C07K 16/44* (2013.01); *G01N 33/558* (2013.01); *C07K 2317/622* (2013.01); *C07K 2317/92* (2013.01); *G01N 2800/321* (2013.01); *G01N 2800/52* (2013.01)

(58) Field of Classification Search
CPC .............. C07K 16/44; C07K 2317/622; C07K 2317/92; G01N 33/558; G01N 33/9453; G01N 2800/321; G01N 2800/52
See application file for complete search history.

(56) References Cited

U.S. PATENT DOCUMENTS

| | | |
|---|---|---|
| 2007/0196510 A1 | 8/2007 | Gerber et al. |
| 2010/0098688 A1 | 4/2010 | Schulze-Forster et al. |
| 2013/0330352 A1 | 12/2013 | Akita et al. |
| 2014/0170158 A1 | 6/2014 | Neptune et al. |
| 2014/0248315 A1 | 9/2014 | Dow et al. |
| 2014/0349862 A1 | 11/2014 | Trieu |
| 2015/0072022 A1 | 3/2015 | Kiefer |
| 2015/0147823 A1 | 5/2015 | Trieu |
| 2015/0284471 A1 | 10/2015 | Meininger et al. |
| 2015/0366909 A1 | 12/2015 | Faustman |
| 2016/0199354 A1 | 7/2016 | Trieu |

FOREIGN PATENT DOCUMENTS

| | | |
|---|---|---|
| WO | 2012/166795 A1 | 12/2012 |
| WO | 2013/147462 A1 | 10/2013 |
| WO | 2015/154091 A1 | 10/2015 |

OTHER PUBLICATIONS

Matalka et al. Enzyme linked immunosorbent assay for determination of amlodipine in plasma. J. Clin. Lab. Analysis 2001, vol. 15, pp. 47-53.*
Geertruida et al. Lateral flow (immuno)assay: its strengths, weakness, oppoetunities and threats. A literature survey. Anal. Bioanal. CHem. 2009, vol. 393, pp. 569-582.*
Westermann et al. Simple, rapid and sensitive determination of epinephrine and norepinephrine in urine and plasma by noncompetitive enzyme immunoassay, compared with HPLC method. CLic. Lab. 2002, vol. 48, pp. 61-71.*
Jyothirmai et al. Development and validation of an RP-HPLC method for the determination of olmesartan in human plasma. International Journal of Research Pharmacy and Chemistry 2014, vol. 4, No. 2, pp. 457-466.*
Nolli et al. Antibodies against the antibiotics: an overview. Ann. Ist. Super, Sanita., 1991, vol. 27, No. 1, pp. 149-154.*
Chin et al. Haptens and monoclonal antibodies for immunoassay of imidazolinone herbicides. J. Argic. Food Cham. 2002, vol. 50, pp. 3380-3389.*
Ianiro, G., et al., "Systematic Review: Sprue-Like Enteropathy Associated With Olmesartan," Alimentary Pharmacology and Therapeutics 40(1):16-23, Jul. 2014.
Ozeki, K., et al., "Telmisartan Inhibits Cell Proliferation by Blocking Nuclear Translocation of ProHB-EGF C-Terminal Fragment in Colon Cancer Cells," PLOS One 8(2):e56770, Feb. 2013, 17 pages.
Seko, Y., "Effect of the Angiotensin II Receptor Blocker Olmesartan on the Development of Murine Acute Myocarditis Caused by Coxsackievirus B3," Clinical Science 110(3)379-386, Mar. 2006.
Shigenaga, A.-I., et al., "Effect of Olmesartan on Tissue Expression Balance Between Angiotensin II Receptor and Its Inhibitory Binding Molecule," Hypertension 52(4):672-678, Oct. 2008; also Data Supplement, 3 pages.
Wakui, H., et al., "Intrarenal Suppression of Angiotensin II Type 1 Receptor Binding Molecule in Angiotensin II-Infused Mice," American Journal of Physiology: Renal Physiology 299(5):F991-F1003, Nov. 2010.
International Search Report and Written Opinion dated Apr. 18, 2017, issued in corresponding International Application No. PCT/US17/12867, filed Jan. 10, 2017, 7 pages.
Final Preliminary Notice of Rejection dated Jun. 28, 2017, issued in corresponding Korean Application No. 10-2016-7002748, filed Jan. 29, 2016, 16 pages.
International Preliminary Report on Patentability dated Jul. 11, 2017, issued in corresponding International Application No. PCT/US2016/012884, filed Jan. 11, 2016, 10 pages.

(Continued)

*Primary Examiner* — Shafiqul Haq
(74) *Attorney, Agent, or Firm* — Christensen O'Connor Johnson Kindness PLLC

(57) ABSTRACT

This disclosure provides compositions, including antibodies or fragments or derivatives thereof, and related devices and methods effective for detecting and quantifying olmesartan in a sample. The compositions, devices, and methods can be applied to improve the effectiveness of hypertension therapy by monitoring a subject's compliance by determining one or more pharmacokinetic parameters of the subject with a point-of-care device after antihypertensive drug administration. In one embodiment, the antihypertensive drug is olmesartan and the pharmacokinetic parameter is AUC.

12 Claims, 11 Drawing Sheets

(56) References Cited

OTHER PUBLICATIONS

Ludden, T.M., et al., "Variability of Plasma Hydralazine Concentrations in Male Hypertensive Patients," Arthritis and Rheumatism 24(8):987-992, Aug. 1981.
Written Opinion dated Mar. 11, 2016, issued in corresponding International Application No. PCT/US2016/012884, filed Jan. 11, 2016, 9 pages.
Yoshida, K., and M. Kohzuki, "Clinical and Experimental Aspects of Olmesartan Medoxomil, a New Angiotensin II Receptor Antagonist," Cardiovascular Drug Reviews 22(4):285-308, 2004.
Search Report completed Aug. 8, 2017, issued in corresponding Taiwanese Application No. 105102921, filed Jan. 29, 2016, 2 pages.

* cited by examiner

COMPOSITION, DEVICE, AND METHOD FOR DETECTING OLMESARTAN AND IMPROVING COMPLIANCE IN TREATING HYPERTENSION

CROSS-REFERENCE TO RELATED APPLICATION

This application claims the benefit of U.S. Provisional Application No. 62/277,406, filed Jan. 11, 2016, which is hereby incorporated by reference in its entirety.

FIELD OF INVENTION

The present disclosure relates to devices and methods for improving the effectiveness of hypertension therapy by monitoring a subject's compliance by determining one or more pharmacokinetic parameters of the subject with a point-of-care device after antihypertensive drug administration.

BACKGROUND

Today hypertension affects approximately one billion people worldwide and is projected to increase to 1.38 billion people by 2019. Hypertension is a condition that is regarded as a risk factor that progresses heart diseases and ultimately causes adverse cardiac symptoms.

Blood pressure control can often be achieved by antihypertensive therapy with one or more drugs. However, despite the prescription of the highest dose of antihypertensive drugs, such as angiotensin receptor blockers (ARBs) (e.g., olmesartan at 40 mg/day), only about 50% of subjects achieve target blood pressure reduction. The variance in effective treatment of hypertension by antihypertensive drug therapy can be due to a subject's compliance with the administration regimen. Non-compliance will oftentimes lead to the inability of a subject to achieve target blood pressure reduction. Furthermore, the literature suggests that resistant hypertension is a result of non-compliance. Therefore, not surprisingly, the failure of a subject to comply with prescribed antihypertensive drug administration regimen leads to ineffective blood pressure reduction and overall ineffectiveness of treatment.

Despite advances in the development of antihypertensive drugs, their formulations, and methods for their administration, a need exists to further improve the clinical effectiveness of the administration of antihypertensive drugs, particularly to address non-compliance. The present disclosure seeks to fulfill this need and provides further related advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the disclosure provides an antibody or antigen-binding fragment or derivative thereof that that binds to olmesartan. In one embodiment, the antibody or antigen-binding fragment or derivative thereof is isolated. In one embodiment, the isolated antibody or antigen-binding fragment or derivative thereof binds to olmesartan with an affinity of at least $1\times10^{-6}$ $K_D$. In one embodiment, the isolated antibody or antigen-binding fragment or derivative thereof binds to olmesartan with an affinity of at least $1\times10^{-9}$ $K_D$. In one embodiment, the antibody or antigen-binding fragment or derivative has a $K_{on}$ at least about $1\times10^4$ and a $K_{off}$ less than about $1\times10^{-3}$. In one embodiment, the antibody or antigen-binding fragment or derivative specifically binds to olmesartan. In one embodiment, the antibody is a monoclonal antibody. In one embodiment, the antigen-binding fragment is an Fab fragment or an $F(ab)_2$ fragment. In one embodiment, the antigen-binding derivative is a single-chain antibody. In one embodiment, the single-chain antibody is a single chain variable fragment (scFv) or single-chain Fab fragment (scFab). In one embodiment, the antibody or antigen-binding fragment or derivative is detectably labeled.

In another aspect, the disclosure provides a lateral flow assay device, comprising:

(a) a sample receiving zone for receiving the liquid sample;

(b) a detection reagent zone in liquid communication with the sample receiving zone and downstream in flow direction from the sample receiving zone, wherein the detection reagent zone comprises a detection reagent deposited thereon, and wherein the detection reagent comprises an anti-olmesartan antibody or antigen-binding fragment or derivative thereof as described herein labeled with a detectable reporting group; and (c) a capture zone in liquid communication with the detection reagent zone and downstream in flow direction from the detection reagent zone, wherein the capture zone comprises a first capture reagent immobilized thereon, wherein the first capture reagent comprises an olmesartan structure capable of binding the detection reagent.

In one embodiment, the capture zone further comprises a second capture reagent immobilized thereon at a position downstream from the first capture reagent, wherein the second capture reagent is an antibody or antibody fragment or derivative capable of binding the detection reagent irrespective of whether the detection reagent is bound to olmesartan.

In one embodiment, the detectable reporting group is selected from colloidal gold, latex particles, colored dyes, paramagnetic and fluorescent particles. In one embodiment, the olmesartan structure is an olmesartan antigen that competes with olmesartan for binding to the detection reagent. In one embodiment, the first capture reagent is an olmesartan protein conjugate. In one embodiment, the distance between the sample receiving zone and the first capture reagent is varied to optimize olmesartan detection sensitivity. In one embodiment, the distance between the sample receiving zone and the first capture reagent is minimized to optimize olmesartan detection sensitivity.

In another aspect, the disclosure provides a method of detecting the presence of olmesartan in a sample, comprising:

contacting the sample to an anti-olmesartan antibody or antigen-binding fragment or derivative thereof, as described herein, under conditions sufficient to permit binding of olmesartan in the sample with the antibody or antigen-binding fragment or derivative thereof; and detecting the binding of the olmesartan to the antibody or antigen-binding fragment or derivative thereof, thereby detecting the presence of olmesartan in the sample.

In one embodiment, the method further comprises quantifying the amount of olmesartan in the sample by quantifying the amount of olmesartan that is bound to the antibody or antigen-binding fragment or derivative thereof. In one embodiment, detecting the presence of olmesartan in the sample is performed in a competitive assay format. In one embodiment, detecting the presence of olmesartan in the sample is performed in a direct or indirect sandwich assay format. In one embodiment, detecting the presence of olmesartan in the sample is performed in a lateral flow assay format. In one embodiment, the lateral flow assay format comprises:

(a) applying a liquid sample comprising olmesartan to a lateral flow assay device, the device comprising:
  (i) a sample receiving zone for receiving the liquid sample;
  (ii) a detection reagent zone in liquid communication with the sample receiving zone and downstream in flow direction from the sample receiving zone, wherein the detection reagent zone comprises a detection reagent deposited thereon, and wherein the detection reagent comprises the anti-olmesartan antibody or antigen-binding fragment or derivative thereof labeled with a detectable reporting group; and
  (iii) a capture zone in liquid communication with the detection reagent zone and downstream in flow direction from the detection reagent zone, wherein the capture zone comprises a first capture reagent immobilized thereon, wherein the first capture reagent comprises an olmesartan structure capable of binding the detection reagent; and
(b) allowing the sample to flow from the sample receiving zone through the detection reagent zone to provide a detection reagent with olmesartan;
(c) allowing the detection reagent with olmesartan to flow through the capture zone, whereby the first capture reagent binds free detection reagent to provide detection reagent bound to the first capture reagent; and
(d) observing the amount of detection reagent bound to the first capture reagent.

In one embodiment, the capture zone further comprises a second capture reagent immobilized thereon at a position downstream from the first capture reagent, wherein the second capture reagent is an antibody or antibody fragment or derivative capable of binding the detection reagent irrespective of whether the detection reagent is bound to olmesartan, and wherein the method comprises (d) observing the amount of detection reagent bound to the first capture reagent relative to the second capture reagent.

In one embodiment, the method further comprises determining the quantity of olmesartan in the sample by quantifying the amount of detection reagent bound by the first capture reagent and the second capture reagent. In one embodiment, wherein quantifying the amount of detection reagent bound to the capture reagents comprises optical density measurement. In one embodiment, the detectable reporting group is selected from colloidal gold, latex particles, colored dyes, paramagnetic and fluorescent particles. In one embodiment, the olmesartan structure is an olmesartan antigen that competes with olmesartan for binding to the detection reagent. In one embodiment, the first capture reagent is an olmesartan-protein conjugate. In one embodiment, the distance between the sample receiving zone and the first capture reagent is varied to optimize olmesartan detection sensitivity. In one embodiment, the distance between the sample receiving zone and the first capture reagent is minimized to optimize olmesartan detection sensitivity. In one embodiment, the method further comprises observing the amount of excess detection reagent bound to the second capture reagent. In one embodiment, further comprises determining the quantity of olmesartan in the sample by quantitating the amount of excess detection reagent bound to the second capture reagent. In one embodiment, the sample is a liquid biological sample. In one embodiment, the liquid biological sample is blood from a subject, wherein the subject was previously administered olmesartan or a prodrug thereof.

In another aspect, the disclosure provides a method for improving the effectiveness of hypertension therapy by determining one or more pharmacokinetic parameters of the subject with a point-of-care device after administration of an antihypertensive drug, the method comprising:

(a) providing for the administration of the antihypertensive drug at a first dose to a subject in need of hypertension therapy;
(b) determining the concentration of the antihypertensive drug in the subject's blood at one or more time points after administration to provide a set of the antihypertensive drug concentration/time data points, wherein the determination of the concentration of the antihypertensive drug is made using a device or by a method described herein;
(c) transforming the set of the antihypertensive drug concentration/time data points to provide one or more pharmacokinetic parameters; and
(d) providing for the administration of the antihypertensive drug at subsequent doses to achieve a target optimal value for the one or more pharmacokinetic parameters.

In one embodiment, the one or more pharmacokinetic parameters are selected from the group consisting of time to maximum concentration ($T_{max}$), concentration maximum ($C_{max}$), area under the curve (AUC), clearance (CL), volume of distribution ($V_d$), apparent volume of distribution during the terminal phase (Vz), apparent volume of distribution during steady state ($V_{ss}$) and combinations thereof. In one embodiment, the one or more pharmacokinetic parameters is area-under-the-curve (AUC).

In one embodiment, the antihypertensive drug is selected from the group consisting of an angiotensin converting enzyme (ACE) inhibitor, an angiotensin II receptor blocker (ARB), a beta-adrenergic receptor blocker, a calcium channel blocker, a direct vasodilator (e.g., thiazide diuretic), an alpha-1-adrenergic receptor blocker, a central alpha-2-adrenergic receptor agonist, and an aldosterone receptor agonist. In one embodiment, the antihypertensive drug is an angiotensin II receptor blocker (ARB) selected from the group consisting of olmesartan, losartan, candesartan, valsartan, irbesartan, telmisartan, eposartan, azilsartan and fimasartan. In one embodiment, the antihypertensive drug is olmesartan In one embodiment, the subject is in need of treatment for hypertension and dyslipidemia, and the method comprises providing for the administration of olmesartan and an anti-dyslipidemia drug. In one embodiment, a single dosage form comprises olmesartan and rosuvastatin. In one embodiment, the hypertension is resistant hypertension. In one embodiment, the subject was previously treated for hypertension with a three-drug regimen comprising a first drug, a second drug, and a third drug, wherein the first drug is a diuretic, and wherein the subject's blood pressure remained elevated above an established blood pressure goal following the three-drug regimen.

In one embodiment, the second and the third drugs are selected from the group consisting of angiotensin converting enzyme inhibitors, angiotensin II receptor blockers, beta-adrenergic receptor blockers, calcium channel blockers, direct vasodilators, alpha-1-adrenergic receptor blockers, central alpha-2-adrenergic receptor agonists, and aldosterone receptor agonists. In one embodiment, the first, second, and third drugs were administered at a highest approved dose.

In another aspect, the disclosure provides a kit comprising the isolated antibody or antigen-binding fragment or derivative thereof as described herein.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

Figure 1:
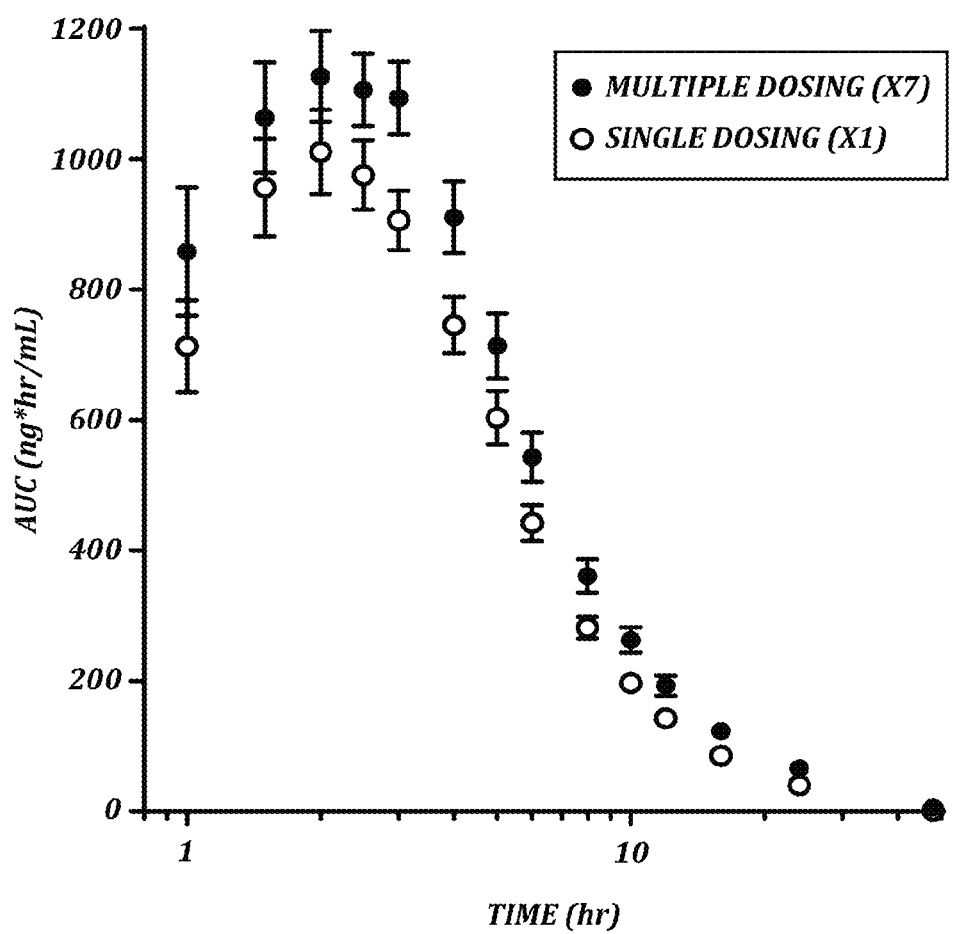
FIG. 1 compares olmesartan AUC (area-under-the-curve) for subjects taking olmesartan regularly for 7 days (Multiple Dosing ×7, solid circles) and for subjects taking olmesartan only 1 day (Single Dosing ×1, open circles): mean+/−95% confidence interval (CI) for subjects taking olmesartan regularly for 7 days. A decrease in olmesartan blood concentration is demonstrated for non-compliance.

The present disclosure provides compositions, methods, devices and kits for detecting and quantifying hypertension drugs in a sample. In one aspect, the compositions, methods, devices and kits are useful for detecting and quantifying olmesartan. The disclosed compositions, methods, devices and kits are useful for improving compliance of hypertension therapy in general and for improving compliance of hypertension therapy with olmesartan. In one aspect, the disclosure provides a method for dosing an antihypertensive drug, such as olmesartan, that utilizes point-of-care monitoring of a subject's blood to determine one or more pharmacokinetic parameter, such as area-under-the-curve (AUC), to improve compliance. In another aspect, the disclosure provides a point-of-care monitoring device for rapid determination of antihypertensive drug concentration in a subject's blood.

The compositions, methods, and devices of the disclosure are effective for improving compliance for resistant hypertension treatment by point-of-care monitoring of the administered antihypertensive drug (e.g., olmesartan) as well as for improving compliance for combined hypertension and dyslipidemia treatment by point-of-care monitoring of the administered antihypertensive and antidyslipidemia drugs (e.g., fixed dose combination of olmesartan and rosuvastatin).

In the practice of the present disclosure, therapeutic drug monitoring is demonstrated to improve effectiveness of achieving blood pressure control in the treatment of hypertension.

Brinker et al., Therapeutic Drug Monitoring Facilitates Blood Pressure Control in Resistant Hypertension, J Am Coll Cardiol. 2014; 63:834-835, describes a study that provides strong support for the use of therapeutic drug monitoring in optimizing blood pressure (BP) control in resistant hypertension (RH). A retrospective analysis of new patients (UTSMC) for RH (2009-2012), 111/397 describes an analysis in which patients met criteria for RH-serum levels of 76 drugs in 40 RH patients were tested by TDM. In the study, 23/40 (58%) of patients had undetectable serum levels of at least one drug screened, indicating medication non-adherence. The TDM-guided adherence counseling led to sustained reduction in BP (from 200±13/121±8 mm Hg to 117±13/75±6 mm Hg) over an average of 25±4 months.

In fact, it is likely that there is no true resistant hypertension due to biological resistant to pharmacological agents, and there is only resistant hypertension due to non-compliance. The methods and devices of the disclosure improve compliance to antihypertensive agent for the treatment of resistant hypertension.

The methods and devices of the disclosure also improve compliance to antihypertensive agent for the treatment of combined (i.e., concomitant) hypertension and dyslipidemia.

Definitive clinical benefits were demonstrated for fixed dose combinations (FDCs) in the treatment of human immunodeficiency virus infection (HIV) and acquired immune deficiency syndrome (AIDS) in the US, a finding that benefited from the backing of the President's Emergency Plan for AIDS Relief. Concurrent treatment of multiple conditions to reduce overall cardiovascular disease-risk lags the multifaceted approach employed for the treatment of HIV/AIDS. In the Optum Database, the five most frequently prescribed pairs of cardiovascular single-agents in 2012 were various combinations of a statin and an antihypertensive agent. Of the five pairs, only amlodipine/atorvastatin FDC is available in the US. The remaining four agent pairs are ACE/statin, beta-blocker/statin, biguanide/statin, and ARB/statin. ARB/statin ranks fifth in usage, with 751 users per 100,000 active enrollees (Wang et al. 2015). Therefore, there is a need for ARB/Statin FDCs, such as ST-101 (fixed dose combination (FDC) of olmesartan, medoxomil, and rosuvastatin calcium).

Hypertension and hyperlipidemia are independent risk factors for the development of premature cardiovascular disease. Several studies indicate that the presence of either condition predisposes an individual to developing the other, and as a result, these two conditions frequently coexist. Of the one billion hypertension patients worldwide, approximately 40% to 50% of patients also have hypercholesterolemia (HCE) (NCEP 2002). Due to the published favorable outcomes associated with effective treatment of either condition, professional organizations in both the US and Canada that issue recommendations for the treatment of hyperlipidemia and hypertension continue to advocate standard therapeutic targets for each condition if optimal reduction of cardiovascular risks is to be achieved. Furthermore, when both risk factors coexist, these professional organizations recommend a more aggressive therapeutic approach to either condition. Hypercholesterolemia is a risk factor for cardiovascular disease, and the benefit of adding a statin to antihypertensive treatment has been well established; conversely, BP control is a necessary component of treatment to decrease blood lipids (ESH/ESCardiology 2013; Joint National Committee 2014; NICE 2011). Additionally, these two risk factors are recognized as synergistic; a 10% reduction in BP along with a 10% reduction in total cholesterol results in a 45% reduction in the incidence of cardiovascular disease (Emberson et al. 2004; Jackson 2005).

Effective simultaneous control of hypercholesterolemia and hypertension is greatly facilitated by FDC as most hypertension patients require multiple medications for effective management. However, adherence to concomitant hypertension and hypercholesterolemia therapy decreases as the number of medications increases. As the pill burden increases, patient adherence rapidly decreases, from 58.8% with one pill to 24.5% with ≥10 pills (Resnic et al. 2006). A single FDC tablet results in 20% higher patient adherence than observed with a 2-tablet combination therapy (Dezii et al. 2000).

Olmesartan is an angiotensin II receptor antagonist and is indicated for the treatment of hypertension. Rosuvastatin is an inhibitor of HMG-CoA reductase and is indicated for the treatment of hypercholesterolemia or mixed dyslipidemia. Besides the pharmacologic plausibility in favor of the combination, there are literature references supporting the combination of these two components in patients with hypertension accompanied with hypercholesterolemia/mixed dyslipidemia (target population). Current practice guidelines recommend the concurrent treatment of reducing BP by inhibiting renin-angiotensin-aldosterone system and lipids, and these recommendations have been adopted in the clinical practice by increasing numbers of co-prescriptions of olmesartan and rosuvastatin. There are now a number of published clinical studies assessing the combination of olmesartan and rosuvastatin, many of which demonstrate that FDCs improve patients' adherence to treatment therapy. Various literature references have shown that the fixed-dose combination of drugs is favorable for patient compliance.

Gupta et al. 2010, Compliance, Safety, and Effectiveness of Fixed-Dose Combinations of Antihypertensive Agents: A Meta-Analysis describes a meta-analysis to assess compliance, persistence, BP control, and safety associated with FDCs in comparison with their free-drug components. There were significant changes (p=0.02) in compliance, but non-significant changes in persistence, BP, and adverse effect.

Bangalore et al. 2007, Fixed-Dose Combinations Improve Medication Compliance: A Meta-Analysis describes that a fixed dose combination resulted in a 26% decrease in the risk of non-compliance compared with free-drug component regimen (p<0.0001). Fixed-dose combination decreases the risk of medication non-compliance and should be considered in patients with chronic conditions like hypertension for improving medication compliance, which can translate into better clinical outcomes.

Gerbino and Shoheiber 2007 describes adherence patterns among patients treated with fixed-dose combination versus separate antihypertensive agents. Adherence rates among patients receiving fixed-dose amlodipine-benazepril versus an ACE inhibitor plus a dihydropyridine calcium channel blockers (CCB) were 87.9% and 69.2%, respectively (p<0.0001), over a mean follow-up of 259 and 247 days, respectively. Fixed-dose amlodipine-benazepril was associated with higher adherence rates versus an ACE inhibitor plus a dihydropyridine CCB taken as 2 separate tablets, regardless of the number of concomitant medications prescribed.

Vanderpoel et al. 2004, Adherence to a Fixed-Dose Combination of Rosiglitazone Maleate/Metformin HCl in Subjects with Type 2 Diabetes Mellitus: A Retrospective Database Analysis described significantly less reduction in the MPR change for the mono-to-FDC cohort compared with the mono-to-dual cohort (−4.6% vs −12.4%; p<0.001). There was significant improvement in the mean MPR change for the dual-to-fixed dose combination therapy (FDCT) cohort compared with the dual-to-dual cohort (3.5% vs −1.3%; p<0.005).

Barner 2011, Adherence to Oral Antidiabetic Agents with Pioglitazone and Metformin: Comparison of Fixed-Dose Combination Therapy with Monotherapy and Loose-Dose Combination Therapy describes a study in which patients (n=60) who switched from loose-dose combination therapy (LDCT) to FDCT, adherence increase significantly by 8.9% (p=0.0081). Those (n=270) who switched from monotherapy (MT) to FDCT had a 9% significant decrease (p<0.0001) in adherence.

ESH/ESC Guidelines 2013, 2013 ESH/ESC guidelines for the management of arterial hypertension indicated that guidelines favor the use of combinations of two antihypertensive drugs at fixed doses in a single tablet, because reducing the number of pills to be taken daily improves adherence, which is unfortunately low in hypertension, and increases the rate of BP control FDC olmesartan plus rosuvastatin Dezii 2000b, A Retrospective Study of Persistence With Single-Pill Combination Therapy vs Concurrent Two-Pill Therapy In Patients With Hypertension describes a study in which at 12 months, the percentages of patients persisting with lisinopril/HCTZ (68.7%) and enalapril/HCTZ (70.0%) therapy were 18.8 percent and 21.7 percent greater, respectively, than the percentages of patients persisting with lisinopril plus concurrent diuretic therapy (57.8%) or enalapril maleate plus concurrent diuretic therapy (57.5%). Statistical significance (p<0.05) was demonstrated at 6 and 12 months for both comparisons.

Pan et al. 2008, Impact of Fixed-Dose Combination Drugs on Adherence to Prescription Medications describes a study in which the FDC enhanced adherence rates by approximately 13% when compared to a 2-pill regimen. Compared to 2-pill therapy, a FDC resulted in important increases in patient adherence. Economic analyses are warranted to determine whether the clinical benefits attributable to the adherence gains are worth the incremental cost of an FDC.

Dickson and Plauschinat 2008, Compliance with Antihypertensive Therapy in the Elderly describes compliance rates were significantly higher with fixed-dose versus free-combination therapy (63.4% vs 49.0%; p<0.0001). The average total costs were reduced by 12.5% for patients using fixed-dose versus free-combination therapy (p<0.003).

Han et al. 2012, Lycemic Effectiveness and Medication Adherence with Fixed-Dose Combination or Co-Administered Dual Therapy of Antihyperglycemic Regimens: A Meta-Analysis describes a meta-analysis that revealed a significantly greater HbA1c reduction with FDC (mean difference [MD]=0.53% [95% CI: 0.78, 0.28]; p<0.0001). Five comparisons described medication possession ratio (MPR) for FDC versus co-administered dual therapy (CDT) cohorts, with significantly higher MPR with FDC (MD=8.6% [95% CI: 1.6, 15.6]; p=0.0162]). Four comparisons examined patients who switched from monotherapy to FDC or CDT, with higher MPR for patients who switched to FDC (MD=7.7% [95% CI: 5.7, 9.6]; p<0.0001). Three comparisons described results for patients who switched from CDT to FDC or stayed on CDT, with higher MPR for patients who switched to FDC (MD=5.0% [95% CI: 3.1, 6.8]; p<0.0001).

Thom et al. 2013, Effects of a Fixed-Dose Combination Strategy on Adherence and Risk Factors in Patients With or at High Risk of CVD describes a study in which the FDC group had improved adherence vs usual care (86% vs 65%; p<0.001) with concurrent reductions in SBP (−2.6 mm Hg; p<0.001) and LDL-C (−4.2 mg/dL; p<0.001) at the end of the study (median follow-up: 15 months). Among patients with or at high risk of CVD, use of an FDC for BP, cholesterol, and platelet control vs usual care resulted in significantly improved medication adherence at 15 months and statistically significant but small improvements in SBP and LDL-C.

Chapman et al. 2010, Association Between Adherence to Calcium-Channel Blocker and Statin Medications and Likelihood of Cardiovascular Events Among US Managed Care Enrollees describes a study in which SPAA patients, 56.5% were adherent at 6 months, compared with 21.4% of the 17,910 CCB/statin patients (p<0.001). Patients receiving SPAA rather than a 2-pill CCB/statin regimen are more likely to be adherent. In turn, adherence to CCB and statin medications is associated with lower risk of CV events in primary prevention patients.

Abbreviations

ACE, angiotensin converting enzyme; BP, blood pressure; CCB, calcium channel blockers; CDT, co-administered dual therapy; CI, confidence interval; CV, cardiovascular; CVD, cardiovascular disease; ESC, European Society of Cardiology; ESH, European Society of Hypertension; FDC, fixed dose combination; FDCT, fixed dose combination therapy; HCl hydrochloride; HCTZ, hydrochlorothiazide; LDCT, loose dose combination therapy; LDL-C, low-density lipoprotein-cholesterol; MD, mean difference; MPR, medication possession ratio; SBP, systolic blood pressure; SPAA, single-pill amlodipine/atorvastatin.

Blood Level of Olmesartan in Increased for Subject that take Olmesartan Regularly for 7 Days Versus those only taking their Drug once.

Drug exposure as AUC was studied among Korean healthy males aged between 20 and 50 years in two clinical studies: (1) taking drug regularly for 7 days (subjects were administered either 1 tablet of 40 mg olmesartan medoxomil, 1 tablet of 20 mg rosuvastatin calcium, or 1 tablet each of both agents orally every 24 hours for 7 days) and (2) taking drug only one day (58 subjects divided into 2 cohorts and treated over 2 periods; one tablet of ST-101 (FDC olmesartan and rosuvastatin) tablet of 40 mg olmesartan medoxomil/20 mg rosuvastatin calcium was administered once orally as the test drug, or 1 tablet each of 40 mg olmesartan medoxomil and 20 mg rosuvastatin calcium was co-administered once orally as the comparator).

Pharmacokinetic analyses were performed. For PK analyses, blood samples were collected at 0 (pre-dose), 0.5, 2, 2.5, 3, 4, 5, 6, 7, 8, 10, 12, 16, 24, and 48 hr after dosing of olmesartan either as FDC or as single agent. The results are graphically illustrated in FIG. 1. FIG. 1 compares olmesartan AUC (area-under-the-curve) for subjects taking olmesartan regularly for 7 days (Multiple Dosing ×7, solid circles) and for subjects taking olmesartan only 1 day (Single Dosing ×1, open circles): mean+/−95% confidence interval (CI) for subjects taking olmesartan regularly for 7 days. A decrease in olmesartan blood concentration is demonstrated for non-compliance.

Differences between Compliance and Non-Compliance Across a 24 hr Pperiod.

The differences between compliance and non-compliance across a 24 hr period were determined (see Table 1). The % reduction in blood concentration can be used to determine if the patient is missing his/her medication. As described above, pharmacokinetics (AUC) demonstrates that olmesartan exhibits a rapid clearance with much of the drug gone from the system at 48 hr. There is about 40 ng/mL remaining at 24 hr, which accumulated to about 60 ng/mL following consistently medication for 7 days. The comparison between full compliance for 7 days versus noncompliance is tabulated below.

TABLE 1 olmesartan in blood for compliant vs non-compliant dosing

| Time (hrs) | Blood concentration (ng/mL)/Compliance-7X | Blood concentration (ng/mL)/Non-Compliance-1X | % Reduction |
| --- | --- | --- | --- |
| 0 | 54.14927536 | 0 | Infinity |
| 1 | 858.4608696 | 676.8221239 | 26.84% |
| 1.5 | 1063.713043 | 931.8646018 | 14.15% |
| 2 | 1126.868116 | 1002.265487 | 12.43% |
| 2.5 | 1106.507246 | 976.3982301 | 13.33% |
| 3 | 1093.913043 | 911.8318584 | 19.97% |
| 4 | 910.9130435 | 760.0176991 | 19.85% |
| 5 | 713.5072464 | 616.6283186 | 15.71% |
| 6 | 543.3913043 | 452.2035398 | 20.17% |
| 8 | 360.942029 | 288.8672566 | 24.95% |
| 10 | 263 | 201.6814159 | 30.40% |
| 12 | 192.6811594 | 146.0778761 | 31.90% |
| 16 | 123.2144928 | 87.87433628 | 40.22% |
| 24 | 66.24057971 | 41.05929204 | 61.33% |

The results show that it is clear that knowing the blood concentration of the individual patient following the first initial dose will allow determination if the patient is taking his/her medication regularly. Full compliance will result in medication level at the described time being higher than the initial dose value by the specified amount listed in the above table.

Furthermore, the differences expanded the further out the medication is taken with maximal differences observed at 24 hr post dose (0 hr of next dose—for once daily dosing).

The time the medication is taken can be self-reported by the patient and confirmed by repeated measurement in the doctor office if necessary. Repeated blood quantitation prior to Tmax would have an upward slope and repeated blood quantitation following Tmax would have a downward slope with the steepness determine by whether the collection time was within the initial clearance (alpha-phase) or the late clearance (beta-phase).

The data demonstrates that compliance can be assessed by measuring a pharmacokinetic parameter (e.g., AUC) at a time (e.g., 24 hour) remote from the time the last dose was taken. The present disclosure provides methods and devices for assessing compliance by facilitating rapid point-of-care measurement of one or more pharmacokinetic parameters.

The present disclosure addresses the need for improved hypertensive treatment and treatment monitoring due to high variability of hypertensive drug when dosed at mg/day, which results in highly variable blood pressure reduction and poor correlation between dose and blood pressure reduction. The present disclosure provide for compositions, devices, and methods of treating resistant hypertension. For example, in the methods, a AUC dosing regimen assisted by point-of-care quantitation device for olmesartan is provided. In the methods, PK parameters are determined from first dosing to predict PK quantitation of subsequent dosing. Because there is dose proportionality, a linear equation can be derived that determines the necessary dose adjustment to achieve target AUC.

Olmesartan Antibodies

Olmesartan is an angiotensin II receptor antagonist that has been used for the treatment of high blood pressure. Olmesartan is typically administered as an ester prodrug that rapidly hydrolyzes into the corresponding acid (RNH-6270; see Formula I).

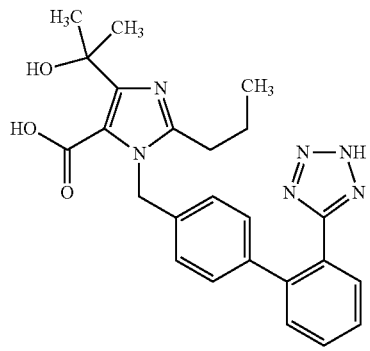

Formula I

As used herein, the term olmesartan refers to the structure set forth in Formula I. Production of antibodies against olmesartan has been a challenge. Without being bound by theory, it is believed that the relative size of olmesartan renders it unavailable as an antigen in vertebrate immune systems for natural production of antibodies. This is illustrated in the observed difficulty producing polyclonal goat antibodies against olmesartan, as described in Example 1. Because the art would benefit from convenient reagents to detect olmesartan, the inventors endeavored to design a conjugate containing olmesartan to produce monoclonal antibodies with binding affinity to olmesartan. With the conjugation of BSA via the carboxylic acid group, the inventors succeeded in producing novel monoclonal antibodies to olmesartan that have affinity to the unbound drug. See Examples 1 and 3.

Accordingly, in one aspect, the disclosure provides compositions, including antibodies, or antigen-binding fragment or derivative thereof, that bind to olmesartan.

As used herein, the term "antibody" encompasses antibodies and antibody fragments thereof, derived from any antibody-producing mammal (e.g., mouse, rat, rabbit, camelid, and primate, including human) or synthetically or recombinantly produced, that specifically binds to a target of interest (e.g., olmesartan) or portions thereof. Exemplary antibodies include polyclonal, monoclonal, and recombinant antibodies; multispecific antibodies (e.g., bispecific antibodies); humanized antibodies; murine antibodies; chimeric, mouse-human, mouse-primate, primate-human monoclonal antibodies; and anti-idiotype antibodies, and may be any intact molecule or fragment thereof, such as an antigen binding fragment. As described herein, monoclonal antibodies are preferable because they provide for increased specificity in binding of the antigen of choice, such as a therapeutic drug (e.g., olmesartan).

As used herein, the term "antigen binding fragment" refers to the antigen binding or variable region from or related to a full-length antibody. Illustrative examples of antibody fragments include Fab, Fab', F(ab)$_2$, F(ab')$_2$, and Fv fragments, scFv fragments, diabodies, nanobodies, linear antibodies, single-chain antibody molecules, and multispecific antibodies formed from antibody fragments.

As used herein, a "chimeric antibody" is a recombinant protein that contains the variable domains and complementarity-determining regions derived from a non-human species (e.g., rodent) antibody, while the remainder of the antibody molecule is derived from a human antibody.

As used herein, a "humanized antibody" is a chimeric antibody that comprises a minimal sequence that conforms to specific complementarity-determining regions derived from non-human immunoglobulin that is transplanted into a human antibody framework. Humanized antibodies are typically recombinant proteins in which only the antibody complementarity-determining regions are of non-human origin.

As used herein, the term "derivative" indicates that the antibody or antibody fragment has been produced from a reference antibody. For example, sometimes it is desirable to modify or enhance binding characteristics of a reference antibody. Thus, the antibody can be subjected to various modifications, including mutations subjected to the encoding DNA, to alter binding properties. The resulting antibody with altered properties is then referred to as a "derivative" of the reference antibody. For example, an antibody derivative can be an antibody that contains mutations resulting from affinity maturation processes that were applied to the reference antibody (or the nucleic acids encoding the reference antibody). Such mutations can result in antibodies with altered (e.g., improved) binding affinity, selectivity, and the like. The term "derivative" also encompasses modifications that combine fragments of antibodies together in, for example, single chain fragments. As used herein, a "single-chain Fv" or "scFv" antibody fragment comprises the $V_H$ and $V_L$ domains of an antibody, wherein these domains are present in a single polypeptide chain. Generally, the Fv polypeptide further comprises a polypeptide linker between the $V_H$ and $V_L$ domains, which enables the scFv to form the desired structure for antigen binding.

Production of antibodies can be accomplished using any technique commonly known in the art. For example, the production of a polyclonal antibody can be accomplished by administering an immunogen containing the antigen of interest (e.g., olmesartan) to an antibody-producing animal. For example, the antigen of interest (also referred to as "target antigen", e.g., olmesartan) can be administered to a mammal (e.g., a rat, a mouse, a rabbit, a chicken, cattle, a monkey, a pig, a horse, a sheep, a goat, a dog, a cat, a guinea pig, a hamster) or a bird (e.g., a chicken) so as to induce production of a serum containing an antigen-specific polyclonal antibody. It is preferred that the olmesartan be administered as part of a conjugate with a carrier protein to facilitate antibody production. The target antigen can be administered in combination with other components known to facilitate induction of a B-cell response, such as any appropriate adjuvant known in the art. Furthermore, the polyclonal antibody reagent can be further processed to remove or subtract any antibody members that have unacceptable affinity for antigens that are not the antigen of interest. The resulting polyclonal antibody reagent will exhibit enhanced specificity for the antigen of interest and are useful for detection and quantification purposes. Many approaches for adsorption of polyclonal antibody reagents to reduce cross-reactivity exist, are familiar to persons of ordinary skill in the art, and are encompassed by the present disclosure.

However, in light of the difficulty of producing acceptable polyclonal antibodies to olmesartan, even when conjugated to a carrier protein, monoclonal antibodies may be preferred. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981), incorporated herein by reference in their entireties. The term "monoclonal antibody" refers to an antibody that is derived from a single clone, including any eukaryotic, prokaryotic, or phage clone, and not the method by which it is produced. Methods for producing and screening for specific antibodies using hybridoma technology are routine and well known in the art.

Antibody fragments that recognize specific epitopes can be generated by any technique known to those of skill in the art. For example, Fab and F(ab')$_2$ fragments of the invention can be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CHI domain of the heavy chain. Further, the antibodies of the present invention can also be generated or modified using various phage display methods known in the art.

Specific, representative examples of the production, processing, purification, characterization, and optimization of olmesartan antibodies useful in the assay methods of the disclosure are described in Example 1.

In some embodiments, the antibody, or antigen-binding fragment or derivative thereof, that binds to olmesartan is isolated, meaning having cellular components of cells producing the antibody or antigen-binding fragment or derivative thereof substantially removed therefrom.

In some embodiments, the antibody or antigen-binding fragment or derivative binds to olmesartan with at least a minimal affinity so as to be useful in an immunoassay to provide a detectable signal enabling detection and/or quantification of the olmesartan in a sample. In some embodiments, the antibody or antigen-binding fragment or derivative binds to olmesartan with an affinity of at least $1 \times 10^{-6}$ $K_D$, such as $1 \times 10^{-6}$ $K_D$, $5 \times 10^{-6}$ $K_D$, $1 \times 10^{-7}$ $K_D$, $5 \times 10^{-7}$ $K_D$, $1 \times 10^{-8}$ $K_D$, $5 \times 10^{-8}$ $K_D$, $1 \times 10^{-9}$ $K_D$, $5 \times 10^{-9}$ $K_D$, $1 \times 10^{-10}$ $K_D$, $5 \times 10^{-10}$ $K_D$, $1 \times 10^{-11}$ $K_D$, $5 \times 10^{-11}$ $K_D$, $1 \times 10^{-12}$ $K_D$, and $5 \times 10^{-12}$ $K_D$, and any threshold therebetween. In an exemplary embodiment, the antibody or antigen-binding fragment or derivative binds to olmesartan with an affinity of at about $1 \times 10^{-9}$ $K_D$ to about $1 \times 10^{-10}$ $K_D$. In some embodiments, with respect to binding olmesartan, the antibody or antigen-binding fragment or derivative has a $K_{on}$ greater than about $1 \times 10^4$ and a $K_{off}$ less than about $1 \times 10^{-3}$, as described in more detail with respect to the related methods. The binding parameters can be in the context of free olmesartan or olmesartan bound to a carrier protein.

Representative Point-of-Care Assay Methods and Devices

The present disclosure also provides a point-of-care (POC) therapeutic drug monitoring (TDM) methods, devices, and related compositions for pharmacokinetic (PK)-guided dosing of therapeutic drugs.

This, in one aspect, the disclosure provides compositions, methods, and devices for immunoassays in general, and compositions, methods, and devices for immunoassay of olmesartan in particular. The compositions, methods, and devices of the disclosure provide information useful for making adjustments to the therapeutic regime for the subject.

The assay compositions, methods, and devices provided herein are described in the context of compositions, methods, and devices for the detection and monitoring of olmesartan. However, it is appreciated that the format of the described compositions, methods, and devices are not so limited, and are readily applied more generally to monitoring any analyte of choice including other antihypertensive drugs.

The present disclosure provides assay compositions, methods, and devices for detecting or quantifying analytes (e.g., olmesartan) in a sample.

The methods and devices can be used to assay a biological sample, such as a sample obtained from a subject (e.g., human patient or mammalian model organism) that has received a therapeutic agent (e.g., olmesartan) for the treatment of a condition. The sample used in the assay is ultimately a liquid sample (e.g., blood, plasma, urine, and the like).

The methods of the disclosure are solid phase assays and therefore are suited for adaptation to other solid phase assay configurations. To exemplify the innovation, the methods and devices are described using a lateral flow assay configuration. It will be appreciated that other solid phase assays know in the art can be configured in accordance with the present methods and devices.

Lateral flow assay methods and devices can be used in accordance with the present disclosure. Depending on the format of the lateral flow assay method and device, the assay reagents can be disposed in certain configurations. In such an embodiment, one reagent will act as a "detection reagent" and another reagent will act as a "capture reagent." Within this format, the detection reagent is generally deposited on the conjugate pad at a location between the sample port and a location where the capture reagent is deposited. The detection reagent generally comprises a detectable label, whereas the capture reagent is immobilized in its location on the pad. Thus, during operation, a liquid sample introduced in the sample port can flow along the pad. The sample will come into contact with the detection reagent first, and then subsequently flow over the capture reagent.

Figure 2A:
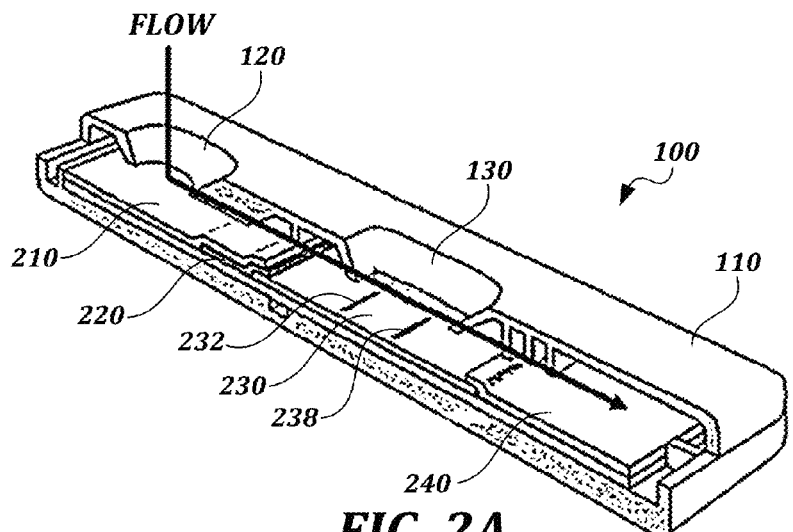
FIG. 2A is an illustration of a representative point-of-care lateral flow assay device of the disclosure useful for rapid therapeutic drug monitoring.

A representative device for performing a lateral flow assay in accordance with the disclosure is illustrated in FIG. 2A. Referring to FIG. 2A, device 100 is a cassette that includes housing 110 having sample port 120, reading window 130, and test strip 200 (see FIG. 2B). In operation, a liquid sample to be analyzed is introduced to the test strip through port 120 and is flowed along the test strip as indicated by the flow direction (from sample pad 210 to absorbent pad 240). The test results can be viewed by observing the test strip through reading window 130.

Figure 2B:
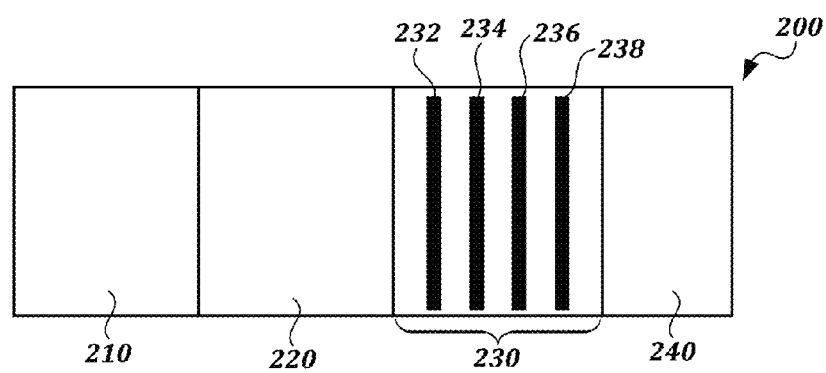
FIG. 2B is an illustration of a representative test strip for the lateral flow assay device illustrated in FIG. 2A.

The test strip includes several zones and reagents for carrying out the assay. Referring to FIGS. 2A and 2B, representative test strip 200 includes sample pad 210, conjugate pad 220, membrane 230, and absorbent pad 240. Sample pad 210, conjugate pad 220, membrane 230, and absorbent pad 240 are in liquid communication such that liquid sample introduced to the sample pad flows through or across the conjugate pad and membrane to the absorbent pad. The size and configuration of the test strip components can be varied to suit the particular assay to be performed. For example, one or more of the component pads and membrane can overlap to facilitate optimal flow from one component to the next (sample pad 210 can overlap with conjugate pad 220, which may overlap with membrane 230, which may overlap with absorbent pad 240, as shown in FIG. 2A). The nature of the test strip zones is not particularly critical and materials for these components are known in the art.

The operation of the representative device is described as follows. Sample pad 210 receives the liquid sample to be tested. Sample flows from sample pad to conjugate pad 220.

Conjugate pad 220 includes one or more detection reagents (e.g., antibodies having an affinity for the analyte in the sample to be assayed and that are labeled to facilitate detection of the antibody in the assay).

In certain embodiments, a single detection reagent is deposited on the conjugate pad. In other embodiments, two or more detection reagents (e.g., two different antibodies, such as first and second antibodies having different affinities for the analyte to be assayed, different $K_{on}$ rates, and/or different $K_{off}$ rates) are deposited on the conjugate pad. The first and second affinities are not the same. In one embodiment, the first $K_{on}$ is greater than the second $K_{on}$. In another embodiment, the second $K_{off}$ is greater than the first $K_{off}$. The description and specification of antibody affinity, $K_{on}$, and $K_{off}$ rates described below in the context of the olmesartan assay are applicable to the assay of therapeutic agents in general. The amount of first and second antibody deposited can be varied and need not be the same.

The detection reagent(s) deposited on conjugate pad 220 are mobilized by the liquid sample and flow with the sample to membrane 230. When analyte is present in the sample, binding between the analyte and detection reagent begins to occur once the sample contacts the detection reagents. Capture of the detection reagents, some of which may include bound analyte and some of which may not, occurs on membrane 230.

Membrane 230 includes a capture zone with at least two distinct capture points: a first capture point for capturing detection reagent that does not include bound analyte (test line T or T1) (see 232 in FIGS. 2A, 2B, 2C, and 2D) and a second capture point for capturing excess detection reagent that does include bound analyte (control line, C) (see 238 in FIGS. 2A, 2B, 2C, and 2D). The first capture point includes a first capture material (e.g., an immobilized antigen) that is effective for capturing the detection reagent that does not include bound analyte (i.e., free detection reagent). The second capture point includes a second capture material (e.g., an immobilized antibody) that is effective for capturing the detection reagent with or without bound analyte. The amount of detection reagent captured by the first and second capture materials, respectively, will depend on the amount of analyte present in the sample. The assay described above is a competitive assay in which the analyte and first capture material compete for affinity binding to the detection reagent. The greater the amount of analyte present in the sample, the lesser the amount of detection reagent captured by the first capture material. Due to depletion of capture material, the lesser the amount of the analyte present in the sample, the more detection reagent being capture by the first capture material and therefore less available for capture by the second capture material. The ratio of the intensity of the first and second capture lines gives the best value for quantitation of the analyte.

In certain embodiments, the capture zone includes two or more first capture points (e.g., 232 and 234 in FIGS. 2B and 2C) for capturing detection reagent that does not include bound analyte. In certain embodiments, the capture zone includes two or more second capture points (e.g., 236 and 238 in FIG. 2B) for capturing detection reagent.

The illustrated approach of the lateral flow cassette can utilize any compatible reader with the appropriate sensitivity for detection of signal from the flow cassette and the ability to calibrate and quantify such a signal. Beneficial features of any reader can include ease of use features, including touch screen, integrated RFID or integrated barcode reader, and the capacity to easily export results, such as to a memory card or USB stick. The reader preferably has pre-installed software facilitating an interface in a selection of languages. The reader preferably has a high memory capacity to facilitate storage of multiple (such as >1000) results and can save >100 distinct test method protocols. The reader can contain connectivity to facilitate its integration into a larger system, such as through LAN or WLAN connectivity to LIS or cloud based data storage and management systems. Finally, multiple USB ports are desirable for additional connectivity capacities, such as to facilitate connection to external printers, and the like.

A representative reader is the Qiagen's Reader ESEQuant LFR (commercially available from Qiagen, Germany), which has been demonstrated as a compatible effective reader for the inclusion of the lateral flow cassette described herein. This reader is a small, portable device with internal rechargeable battery allowing it to operate out in the field and serves the requirements of the point-of-care (POC) device. The lateral flow cassette is scanned using a confocal camera system embedded in the reader. On board image analysis system is fully functional with the bar code reader of the lateral flow cassettes so that analysis method can be easily uploaded to the device.

Detection Reagents.

In certain embodiments, the detection reagent is or comprises at least one antibody, antibody fragment, or antibody derivative, as described herein, for example, the antibody, or fragment or derivative thereof, that binds to olmesartan. The detection reagent is capable of binding the analyte in the sample (e.g., olmesartan) and when the detection reagent does not bind olmesartan in the sample, the detection reagent binds to the capture reagent.

The detection reagents include a moiety or label that can provide a detectable signal capable of reliable quantification. Suitable moieties include those known in the immunoassay art that provide colorimetric, fluorescent, chemiluminescent, enzymatic, or radiometric signals. Representative moieties include that those provide a detectable signal that is visual and may not require instrumentation to read (e.g., colored moieties or enzymes that generate colored moieties or enzymatic). Quantitation is typically achieved through instrumental analysis of the detectable signal. In one embodiment, the detection reagent is an antibody labeled with colloidal gold, which can be visually observed. Other illustrative detectable label useful in the present disclosure include latex particles, colored dyes, paramagnetic and fluorescent particles, as known in the art.

Gold colloids are generated from reduction of gold chloride with a monodisperse nature, which are of a controlled and uniform diameter, such as 40 nm monodisperse colloid. An antibody is conjugated with colloidal gold through passive absorption.

As noted above, in some embodiments, multiple (i.e., more than one type of) antibodies, antibody fragments, or antibody derivatives can be used. In some embodiments, the multiple (distinct) antibodies, antibody fragments, or antibody derivatives are combined and deposited in the same location on the test strip (i.e., conjugate pad). Accordingly, various modifications can be made to the lateral flow format to facilitate or confer various detection properties. For example, to expand the dynamic range of a device, multiple test lines (T1, T2, etc.) with the use of the same or different affinity antibodies, the dynamic range and/or the reproducibility of the assay can be expanded. The description and specification of positioning capture reagents (T/C) on the test strip described below in the context of the representative assay is applicable to positioning of capture reagents in assay of the disclosure in general.

The preparation of representative detection reagents useful in the assays of the disclosure are described in the Examples.

Capture Reagents.

The capture reagents serve to capture the detection reagent allowing for observation and quantitation of a detectable signal in the assay. As noted above, the assay methods and devices include first and second capture materials immobilized at first and second capture points, respectively.

In one embodiment, the capture reagent is an immobilized analyte (e.g., olmesartan complex), which is an immobilized antigen when the detection reagent is an antibody, that captures detection reagent that does not include bound analyte. The immobilized analyte can be directly immobilized to the test strip. Alternatively, the immobilized analyte can be immobilized via a linker or carrier material (e.g., analyte conjugated to a carrier protein, such as albumin). In such an embodiment, the capture reagent is the first capture material as described above.

In one embodiment, the capture reagent is an immobilized antibody that captures detection reagent that captures detection reagent irrespective of whether the detection reagent is bound with the analyte (e.g., olmesartan). In embodiments in which the detection reagent is a mouse monoclonal antibody, such as described below in the Examples, the capture reagent is an anti-mouse antibody (e.g., goat anti-mouse antibody, GAM antibody). In such an embodiment, the capture reagent is the second capture material as described above.

The preparation of representative capture reagents useful in the assays of the disclosure are described in the Examples.

Alternative Assay Configurations.

The lateral flow assay of the disclosure described herein is a solid phase immunoassay. The lateral flow assay can also be run in a liquid phase format, as described in more detail in Example 3. Briefly, instead of drying the detection agent to the strip downstream of the sample receiving zone and upstream of the capture zone, the detection reagent can be added to the liquid sample and applied to the sample pad as a combined liquid.

It will also be appreciated that the format of the assay and device can be inverted from the format described above such that the detection reagent is the labeled antigen and the capture reagent is the one or more antibody, antibody fragment, or antibody derivative (i.e., immobilized in the capture zone at one or more points). In the operation of such a format, the sample flows through/across the deposited labeled antigen (in a solid phase format) and subsequently contacts the immobilized antibody, antibody fragment, or antibody derivative. At that point, the free analyte (e.g., olmesartan) initially present in the sample competes with the labeled antigen for binding to the immobilized antibody, antibody fragment, or antibody derivative. As above, the device can include multiple, distinct antibodies, antibody fragments, or antibody derivatives immobilized at the same or different locations. The capture reagent can be at the same or different locations. In all embodiments where the test strip has multiple locations where capture reagent is immobilized, an appropriate reader is used that can detect signal in those locations.

It is noted that the present devices, systems, compositions, and methods are generally described herein in terms of a lateral flow assay. However, the general strategy for monitoring an antigen of choice (e.g., olmesartan) as described herein does not need to be limited to lateral flow assay formats, but can be applied to other assay formats, such as other solid phase immunoassays (surface plasmon resonance assays), direct or indirect sandwich assay (ELISAs), and the like, which are generally well-known in the art. Accordingly, notwithstanding description addressing lateral flow format, the present disclosure also encompasses devices, systems, compositions, and methods that incorporate any known assay format. In some embodiments, the assay format includes immobilization of capture reagents, such as the antigen conjugate (e.g., olmesartan conjugate) or antigen binding reagents (e.g., anti-olmesartan antibodies, fragments, derivatives) on a substrate. The substrate can be any known appropriate substrate for an assay format, such as nitrocellulose or glass. In some embodiments, the substrate is a nanostructure. In some embodiments, the substrate can comprise or consist of carbon nanostructures, such as carbon nanotubes, to which the capture reagents can be immobilized.

Representative Olmesartan Assay.

Figure 2C:
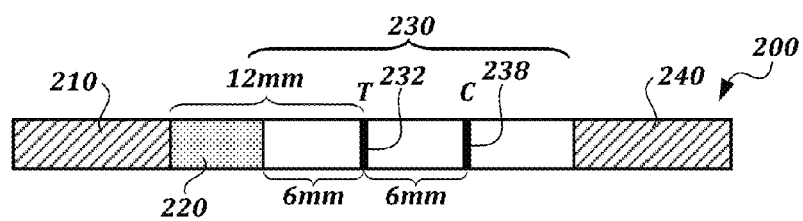
FIG. 2C is an illustration of a representative test strip for the lateral flow assay device illustrated in FIG. 2A. The test strip has a single test line (T) and a single control line (C).
Figure 2D:
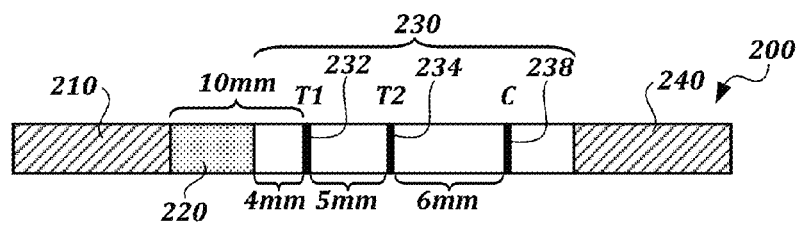
FIG. 2D is an illustration of a representative test strip for the lateral flow assay device illustrated in FIG. 2A. The test strip has two test lines (T1 and T2) and a single control line (C).

FIGS. 2C and 2D are illustrations of representative test strips for an olmesartan lateral flow immunoassay in accordance with the disclosure. Referring to FIG. 2C, representative test strip 200 includes sample pad 210, conjugate pad 220, membrane 230 with first a first capture point 232 (T) and second capture point 238 (C), and absorbent pad 240. Referring to FIG. 2D, representative test strip 200 includes sample pad 210, conjugate pad 220, membrane 230 with first capture points 232 and 234 (T1 and T2) and second capture point 238 (C), and absorbent pad 240. As noted above with regard to FIGS. 2A and 2B, sample pad 210, conjugate pad 220, membrane 230, and absorbent pad 240 are in liquid communication such that liquid sample introduced to the sample pad flows through or across the conjugate pad and membrane to the absorbent pad; the size and configuration of the test strip components can be varied to suit the olmesartan assay to be performed (e.g., one or more of the component pads and membrane can overlap to facilitate optimal flow from one component to the next, as shown in FIG. 2A).

In one embodiment, the disclosure provides a method for assaying (e.g., detecting and/or quantifying) olmesartan in a liquid sample, comprising:

contacting the sample to an anti-olmesartan antibody or antigen-binding fragment or derivative thereof, as described, under conditions sufficient to permit binding of olmesartan in the sample with the antibody or antigen-binding fragment or derivative thereof; and detecting the binding of the olmesartan to the antibody or antigen-binding fragment or derivative thereof, thereby detecting the presence olmesartan in the sample.

In some embodiments, the method further comprises quantifying the amount of olmesartan in the sample by quantifying the amount of olmesartan is bound to the antibody or antigen-binding fragment or derivative thereof.

As described above, the method can be performed in any applicable assay format. For example, in one embodiment, detecting the presence olmesartan in the sample is performed in a competitive assay format. In one embodiment, detecting the presence olmesartan in the sample is performed in a direct or indirect sandwich assay format.

In a preferred embodiment, detecting the presence olmesartan in the sample is performed in a lateral flow assay format. In further embodiments, the lateral flow assay comprises (a) applying a liquid sample comprising olmesartan to a lateral flow assay device, the device comprising:
  (i) a sample receiving zone for receiving the liquid sample;
  (ii) a detection reagent zone in liquid communication with the sample receiving zone and downstream in flow direction from the sample receiving zone, wherein the detection reagent zone comprises a detection reagent deposited thereon, and wherein the detection reagent comprises the anti-olmesartan antibody or antigen-binding fragment or derivative thereof labeled with a detectable reporting group; and
  (iii) a capture zone in liquid communication with the detection reagent zone and downstream in flow direction from the detection reagent zone, wherein the capture zone comprises a first capture reagent immobilized thereon, wherein the first capture reagent comprises an olmesartan structure capable of binding the detection reagent; and (b) allowing the sample to flow from the sample receiving zone through the detection reagent zone to provide a detection reagent with olmesartan;

(c) allowing the detection reagent with olmesartan to flow through the capture zone, whereby the first capture reagent binds free detection reagent to provide detection reagent bound to the first capture reagent; and (d) observing the amount of detection reagent bound to the first capture reagent.

In one embodiment, the capture zone further comprises a second capture reagent immobilized thereon (e.g., a control line) at a position downstream from the first capture reagent, wherein the second capture reagent is an antibody or antibody fragment or derivative capable of binding the detection reagent irrespective of whether the detection reagent is bound to olmesartan. In this embodiment, the method comprises in step (d) observing the amount of detection reagent bound to the first capture reagent relative to the second capture reagent.

In certain embodiments, the method further comprises determining the quantity of olmesartan in the sample by quantifying the amount of detection reagent bound to the first capture reagent. Quantifying the amount of detection reagent bound to the first capture reagent includes optical density measurements, among other methods known and used in the art.

Suitable detectable reporting groups are described above. In one embodiment, the detectable reporting group is colloidal gold. Other illustrative detectable reporting groups include latex particles, colored dyes, paramagnetic and fluorescent particles.

In some embodiments, the antibody or antigen-binding fragment or derivative binds to olmesartan with an affinity of at least $5 \times 10^{-5}$ $K_D$, as described in more detail above.

The olmesartan antibody, or fragment or derivative thereof, useful in the present methods have a $K_{on}$ greater than about $1 \times 10^4$. Representative $K_{on}$ values are greater than about $2 \times 10^4$, $4 \times 10^4$, $8 \times 10^4$, $1 \times 10^5$, $1 \times 10^6$, and $1 \times 10^7$). Preferred ranges are from about $1 \times 10^4$ to about $1 \times 10^7$.

The olmesartan antibody, or fragment or derivative thereof, useful in the present methods have a $K_{off}$ less than about $1 \times 10^{-3}$. Representative $K_{off}$ values are less than about less than about $1 \times 10^{-3}$, $1 \times 10^{-4}$, $1 \times 10^{-5}$, and $1 \times 10^{-7}$. Preferred $K_{off}$ values range from about $1 \times 10^{-3}$ to $1 \times 10^{-7}$.

In certain embodiments, the olmesartan antibody, or fragment or derivative thereof, has a $K_{on}$ from about $1 \times 10^4$ to about $1 \times 10^6$ and a $K_{off}$ from about $1 \times 10^{-3}$ to about $1 \times 10^{-4}$.

In one embodiment, the antibody has a high $K_{on}$ and low $K_{off}$ (e.g., minimum $K_{on}$ is $2.0 \times 10^5$ and maximum $K_{off}$ is $1.0 \times 10^{-3}$). In this embodiment, the capture line is placed at 0.0 to 0.4 T/C. For this class, monoclonal antibody engineering would focus on keeping $K_{off}$ constant while increasing $K_{on}$ as much as possible. The greater the $K_{on}$ the better is the antibody detection.

In another embodiment, the antibody has a low $K_{on}$ and high $K_{off}$ (e.g., minimum $K_{on}$ is $2.0 \times 10^4$ and maximum $K_{off}$ is $2.0 \times 10^{-4}$. In this embodiment, the capture line is placed at 0.2-1.0 T/C. For this class, monoclonal antibody engineering would focus on keeping $K_{on}$ constant while decreasing $K_{off}$ as much as possible. The lower the off rate the better is the antibody for detection.

In the assay, the first capture point includes an immobilized olmesartan structure that serves as an olmesartan antigen that competes with olmesartan for binding to the detection reagent. The first capture point captures detection reagent that does not include bound olmesartan (i.e., free detection reagent). In certain embodiments, the olmesartan material is an olmesartan protein conjugate. Suitable protein conjugates include serum albumin conjugates, such as BSA-olmesartan.

In the assay, the second capture point includes an immobilized antibody capable of binding the detection reagent. In certain embodiments, the antibody is a goat anti-mouse antibody.

As noted above, the olmesartan detection sensitivity in the assay can be optimized by varying the distance between the point at which the sample is introduced to the lateral flow device (e.g., sample receiving zone) and the first capture reagent. In certain embodiments, the distance between the sample receiving zone and the first capture reagent is minimized to optimize olmesartan detection sensitivity. In certain embodiments, the distance is less than 20 mm, less than 10 mm, less than 5 mm, less than 3 mm, less than 2 mm, or less than 1 mm. In certain embodiments, the distance is from 20 to 1 mm, 10 to 1 mm, 5 to 1 mm, 3 to 1 mm, or 2 to 1 mm.

The optimization can be described as relative positioning of T (test line) and C (control line): T/C, which is defined as the distance from origin to T/distance from origin to C ratio, where the origin is defined as the upstream edge of the capture zone (upstream edge of membrane 230 in FIGS. 2A-2D). T/C can be greater than about 0.0 (i.e., first capture reagent is located at upstream edge of capture zone), or about 0.01, about 0.02, about 0.04, about 0.08, about 0.10, about 0.20, about 0.40, about 0.80, or less than about 1.0 (i.e., first capture reagent is located at the downstream edge of the capture zone, with second capture reagent located intermediate the first capture reagent and the downstream edge of the capture zone). Preferably, T/C is from about 0.2 to about 0.7.

In certain embodiments, the ratio of the first distance to the second distance is from about 0.0 to about 0.40. In other embodiments, the ratio of the first distance to the second distance is from about 0.20 to about 1.0.

In certain embodiments, the amount of excess detection reagent that is bound to the second capture reagent is observed and measured. In certain embodiments, determining the quantity of olmesartan in the sample is determined by relating the final capture reagent (test line) to the second capture reagent (control line).

As noted above, representative assay of the disclosure can include more than one first capture reagents in more than one first capture points. In certain of these embodiments, the method further includes a third capture point (see T2, 234 in FIG. 2D) intermediate the first (T1, 232 in FIG. 2D) and second (C, 238 in FIG. 2D) capture point, wherein the third capture point comprises an olmesartan material capable of binding the detection reagent. The olmesartan material in the first and third points can be the same or different. In certain of these embodiments, the quantity of olmesartan in the sample is determined by quantitating the amount of detection reagent bound to the first and second capture reagents. Quantitating the amount of detection reagent bound to the first and second capture reagents can include optical density measurement.

In certain embodiments of the method, the lateral flow device further comprises an absorbent zone in liquid communication with the capture reagent zone and downstream in flow direction from the capture reagent zone.

It is noted that the methods and devices of the disclosure are useful for detecting levels of olmesartan in a biological sample.

The description of a representative lateral flow immunoassay in accordance with the methods and devices of the disclosure is described in Example 2.

Antihypertensive Drug Dosing by Pharmacokinetic Parameter

In additional aspects, the disclosure provides methods for treating hypertension by administering an antihypertensive drug in general, and olmesartan or olmesartan/rosuvastatin FDC in specific, and monitoring the subject's compliance with the prescribed dosing regimen. As used herein, the term "administering" includes direct administration to the subject as well as providing for the administration, e.g., prescribing olmesartan to the subject with instructions for administration (e.g., self-administration).

In the method, a dosing regimen targeting one or more specific pharmacokinetic parameters (e.g., AUC) is provided in which the one or more pharmacokinetic parameters are determined from first dosing with an antihypertensive drug and is used to adjust subsequent dosing to achieve the targeted PK parameter. The targeted PK (AUC) dosing regimen for olmesartan was made possible by our discovery of: (1) the targeted AUC value derived from our olmesartan pharmacokinetic studies; (2) the ability to predict subsequent AUCs by AUC after first dose; and (3) the method of adjustment taking advantage of our demonstration of olmesartan dose proportionality when dosed as either olmesartan or as olmesartan/rosuvastatin FDC.

Hypertension Therapy Efficacy Improvement by Monitoring Patient Compliance

In one aspect, the disclosure provides a method for improving the effectiveness of hypertension therapy by monitoring the level of olmesartan in the subject after administration. In one embodiment, this is a method of monitoring a subject's compliance to the drug regimen by determining one or more pharmacokinetic parameters of the subject with a point-of-care device after administration of an antihypertensive drug (e.g., olmesartan). In one embodiment, the method comprises:

(a) providing for the administration of olmesartan at a first dose to a subject in need of hypertension therapy;

(b) determining the concentration of olmesartan in the subject's blood at one or more time points after administration to provide a set of olmesartan concentration/time data points, wherein the determination of the concentration of olmesartan is made using a device of as described herein or by a method as described herein;

(c) transforming the set of antihypertensive drug concentration/time data points to provide one or more pharmacokinetic parameters; and (d) providing for the administration of olmesartan at subsequent doses to achieve a target optimal value for the one or more pharmacokinetic parameters.

Any suitable pharmacokinetic (PK) parameter or parameters can be used in accordance with this aspect of the disclosure, including, without limitation, concentration, concentration time course, peak concentration, and time after administration to peak concentration, terminal half-life, area-under-the-curve (AUC), bioavailability, absorption, distribution, metabolism, excretion, biotransformation, or a combination thereof.

As used herein, the phrase "transforming the concentration/time data points" refers to the application of mathematical operations, formulas, theories, and/or principles (e.g., a formula for calculating AUC) to the concentrations/time data points of the individual subject to provide the pharmacokinetic value (e.g., AUC).

The target pharmacokinetic value is pre-determined by statistical analysis from a population of subjects receiving the antihypertensive drug at its optimal dose. The term "optimal dose" refers to a dose (e.g., mg/day) associated with desirable drug efficacy at lower risk doses of a drug (e.g., the $C_{max}$ range corresponding to patients experiencing high drug efficacy at a low dose) and is determined from a statistical analysis of a subject population receiving doses of the antihypertensive drug for whom there was therapeutic improvement without significant adverse drug reactions or significant side effects. Significant adverse drug reactions refer to ADRs that the subject finds intolerable, impair physiologic functions, and put the subject at risk for immobility and/or death or combinations thereof. Significant side effects refer to side effects that the subject finds intolerable, impair physiologic functions, and put the patient at risk for immobility and/or death or combinations thereof.

As noted above, the target pharmacokinetic parameter is the pre-determined optimal value. In certain embodiments, the target pharmacokinetic parameter is the pre-determined optimal value +/−5%. In other embodiments, the target pharmacokinetic parameter is the pre-determined optimal value +/−2%. In further embodiments, the target pharmacokinetic parameter is the pre-determined optimal value +/−1%. In yet other embodiments, the target pharmacokinetic parameter is the pre-determined optimal value +/−0.5%.

In certain embodiments, the antihypertensive drug is olmesartan and the pharmacokinetic parameter used in the method is area-under-the-curve (AUC).

Area-under-the-curve (AUC) is a pharmacokinetic parameter that is used in the method of the disclosure to dose olmesartan. As used herein, the term "area under the curve (AUC)" is the area under the curve in a plot of concentration of drug in blood plasma as a function of time. Typically, the area is calculated starting at the time the drug is administered and ending when the concentration in plasma is negligible. AUC represents the total drug exposure over time. Assuming linear pharmacodynamics with elimination rate constant K, AUC is proportional to the total amount of drug absorbed by the body (i.e., the total amount of drug that reaches the blood circulation). The proportionality constant is 1/K.

For olmesartan, the target AUC is about 7,000 hr*ng/mL. The target AUC of 7,000 hr*ng/mL was determined from statistical analysis of a subject population receiving olmesartan. The target AUC is the median AUC value determined from a population of subjects receiving olmesartan at a dose of 40 mg/day (daily administration). In certain embodiments, the target AUC is from about 6,000 to about 8,000 hr*ng/mL. In other embodiments, the target AUC is from about 6,500 to about 7,500 hr*ng/mL. In certain embodiments, the target AUC is 7,000 hr*ng/mL+/−5%. In other embodiments, the target AUC is 7,000 hr*ng/mL+/−2%. In further embodiments, the target AUC is 7,000 hr*ng/mL+/−1%. In yet other embodiments, the target AUC is 7,000 hr*ng/mL+/−0.5%.

Because of the dose proportionality, determination of the second dose is straightforward. When the determined pharmacokinetic (PK) parameter is the same as the target PK parameter, the second dose is the same as the first dose. When the determined PK parameter is greater than the target, the second dose is less than the first dose by the same proportion. When the determined PK parameter is less than the target, the second dose is greater than the first dose by the same proportion.

In certain embodiments, the method further comprising repeating steps (a)-(d) until the target pharmacokinetic parameter value(s) and/or blood pressure control is achieved.

The term "blood pressure control" refers to maintenance of blood pressure <150 mm Hg (SBP) and <90 mm Hg (DBP) for subjects >60 years of age, and <140 mm Hg (SBP) and <90 mM Hg (DBP) for subjects <60 years of age.

The method of the disclosure is effective for monitoring compliance of an antihypertensive drug administration regimen. Representative antihypertensive drugs include angiotensin converting enzyme (ACE) inhibitors, angiotensin II receptor blockers (ARBs), beta-adrenergic receptor blockers, calcium channel blockers, direct vasodilators, alpha-1-adrenergic receptor blockers, central alpha-2-adrenergic receptor agonists, and aldosterone receptor agonists. Representative angiotensin II receptor blockers include olmesartan, losartan, candesartan, valsartan, irbesartan, telmisartan, eposartan, azilsartan and fimasartan. In certain embodiments, the antihypertensive drug is olmesartan.

The method of the disclosure is effective for monitoring compliance of hypertension treatments and therefore is effective for treating hypertension.

The above method is also effective for treating subjects suffering from resistant hypertension. In certain embodiments, the subject treatable by the method is a subject that has been previously treated for hypertension with a three-drug regimen in which one of the three drugs (i.e., first drug) is a diuretic, and where the subject's blood pressure remained elevated above an established blood pressure goal following the three-drug regimen. In this method, the second and the third drugs of the three-drug regiment are selected from angiotensin converting enzyme inhibitors, angiotensin II receptor blockers, beta-adrenergic receptor blockers, calcium channel blockers, direct vasodilators, alpha-1-adrenergic receptor blockers, central alpha-2-adrenergic receptor agonists, and aldosterone receptor agonists. In certain embodiments, the first, second, and third drugs were administered at their highest approved dose.

The above method is also effective for treating subjects in need of combined hypertension and dyslipidemia therapy. In certain embodiments, the subject treatable by the method is a subject that is in need of treatment for hypertension and dyslipidemia. In certain embodiments of this method, an antihypertensive drug and an anti-dyslipidemia drug are individually administered. In other embodiments of this method, a single dosage form that comprises an antihypertensive drug and an anti-dyslipidemia drug (e.g., rosuvastatin or a salt thereof) is administered. In certain embodiments of this method, the single dosage form comprises olmesartan and rosuvastatin.

Resistant Hypertension

Although hypertension can be controlled with lifestyle changes and drugs, uncontrolled or resistant hypertension is a significant unmet clinical need in 22 percent of the hypertensive population. Despite a wide range of drugs available for antihypertensive therapy, a segment of the patient population continues to exhibit resistance to a baseline antihypertensive therapy with one or more drugs. A particularly challenging subject population has clinically diagnosed resistant hypertension. Resistant hypertension is defined by the Seventh Report of the Joint National Committee on Prevention, Detection, Evaluation, and Treatment of High Blood Pressure (JNC 7; Chobanian et al. (2003) Hypertension 42:1206-1252) as a failure to achieve goal blood pressure in subjects who are adhering to full doses of an appropriate three-drug regimen that includes a diuretic. Further, resistant hypertension is diagnosed by many physicians on the basis of a subject's resistance to adequate, but less than full doses, of an appropriate three-drug regimen because of the risk or occurrence of adverse events associated with full doses. An "adequate" dose as prescribed by the physician can be less than or equal to a full dose of the drug. A "full" dose or "highest approved dose" is the lowest of (a) the highest dose of the drug labeled for a hypertension indication; (b) the highest usual dose of the drug prescribed according to JNC 7, BHD-IV, ESH/ESC or WHO/ISH guidelines; or (c) the highest tolerated dose of the drug in the particular subject.

As noted above, in certain embodiments, the methods of the disclosure are effective for improving compliance for subject being treated for resistant hypertension.

In certain embodiments, the subject treatable by the methods of the disclosure is a subject that has been previously treated for hypertension with a three-drug regimen in which one of the three drugs (i.e., first drug) is a diuretic, and where the subject's blood pressure remained elevated above an established blood pressure goal following the three-drug regimen. In this method, the second and the third drugs of the three-drug regiment are selected from angiotensin converting enzyme inhibitors, angiotensin II receptor blockers, beta-adrenergic receptor blockers, calcium channel blockers, direct vasodilators, alpha-1-adrenergic receptor blockers, central alpha-2-adrenergic receptor agonists, and aldosterone receptor agonists. In certain embodiments, the first, second, and third drugs were administered at their highest approved dose.

Hypertension and Dyslipidemia

An estimated 40 to 45 percent of hypertensive patients also suffer from dyslipidemia. Because it is considered advantageous to treat patients suffering from hypertension and dyslipidemia with a single therapeutic agent, combinations of therapeutic agents in single dose form have been developed for concomitantly treating both diseases. Combination formulations of antihypertensive and antihyperlipidemic agents are described in WO 95/26188, WO 97/37688, WO 99/11260, WO 00/45818, WO 04/062729, and WO 06/040085. One such single dose form is Caduet™, which is a clinically useful combination formulation of atorvastatin and amlodipine.

Rosuvastatin, an HMG-CoA reductase inhibitor, is useful for the treatment of hypercholesterolemia, hyperlipoproteinemia, and atherosclerosis; and rosuvastatin's calcium salt is commercially available under the designation Crestor™. Olmesartan medoxomil is useful for the treatment of essential hypertension and is commercially available under the designation Benicar™. When a single matrix formulation of rosuvastatin and olmesartan medoxomil is administered, a drug-drug interaction (DDI) between rosuvastatin and olmesartan medoxomil occurs that results in delaying the in vivo release (i.e., dissolution) of rosuvastatin calcium to the gastrointestinal fluid and thus delaying the translocation thereof to the gastrointestinal membrane, inhibiting the absorption of rosuvastatin.

Olmesartan

Olmesartan medoxomil formulations should be designed so as to exhibit high dissolution rate of olmesartan medoxomil in an in vitro comparative dissolution test, in order to obtain a bioequivalent formulation to other single formulations containing olmesartan medoxomil. In order to obtain the high in vitro dissolution rate, olmesartan medoxomil tablet comprises a preferred disintegrant, which may be one or more selected from the group consisting of low substituted hydroxypropyl cellulose, carboxymethylcellulose calcium, croscarmellose sodium, crospovidone, sodium starch glycolate, and pregelatinized starch. In one embodiment, olmesartan medoxomil tablet comprises 7.5 or more % by weight of low substituted hydroxypropyl cellulose, 5 or more % by weight of carboxymethylcellulose calcium, 15 or more % by weight of croscarmellose sodium, 10 or more % by weight of crospovidone, 5 or more % by weight of sodium starch glycolate, or 5 or more % by weight of pregelatinized starch, based on the total weight of the tablet comprising olmesartan medoxomil. In another embodiment, the compartment comprising olmesartan medoxomil comprises 7.5 to 65% by weight of low substituted hydroxypropyl cellulose, 5 to 60% by weight of carboxymethylcellulose calcium, 15 to 30% by weight of croscarmellose sodium, 10 to 40% by weight of crospovidone, 5 to 40% by weight of sodium starch glycolate, or 5 to 60% by weight of pregelatinized starch, based on the total weight of the tablet comprising olmesartan medoxomil. In a further embodiment, the tablet comprising olmesartan medoxomil comprises 7.5 to 65% by weight, preferably 10 to 60% by weight, more preferably about 20±1% by weight of low substituted hydroxypropyl cellulose, based on the total weight of the tablet comprising olmesartan medoxomil.

Olmesartan/Rosuvastatin FDC

An improved pharmaceutical composition that is a single dosage form of olmesartan medoxomil and rosuvastatin or its salts is described in WO 2013/147462. This single dosage form comprises separate compartments for each drug in which each drug is separately and independently formulated. When the single dosage form is administered, the interaction to in vivo absorption is minimized and the combination formulation is bioequivalent to the single formulation of each of the drugs.

In certain embodiments, the subject treatable by the methods of the disclosure is a subject that is in need of treatment for hypertension and dyslipidemia. In certain embodiments of this method, an antihypertensive drug and an anti-dyslipidemia drug are individually administered. In other embodiments of this method, a single dosage form that comprises an antihypertensive drug and an anti-dyslipidemia drug (e.g., rosuvastatin or a salt thereof) is administered. In certain embodiments of this method, the single dosage form comprises olmesartan and rosuvastatin.

A description of representative single dosage forms useful in the methods of the disclosure and methods for making the single dose forms are described in WO 2013/147462, expressly incorporated herein by reference in its entirety. Representative single dose forms useful in the method of the disclosure and a method for making them are described below.

The pharmaceutical composition useful in the methods of the disclosure, which includes olmesartan medoxomil and rosuvastatin or its salt (e.g., rosuvastatin calcium), are formulated into a combination dosage form having separate compartments. That is, the pharmaceutical composition has a single dosage form comprising a compartment comprising olmesartan medoxomil; and a compartment comprising rosuvastatin or its salt, wherein the compartments are formulated in a separate form.

In the pharmaceutical composition, the active ingredients (i.e., olmesartan medoxomil and rosuvastatin or its salt) may be used in a therapeutically effect amount. For example, olmesartan medoxomil may be used in an amount of about 5 mg to about 80 mg, preferably about 10 mg to about 40 mg, in a unit formulation (i.e., unit dosage form); and rosuvastatin or its salt may be used in an amount of about 2 mg to about 40 mg, preferably about 5 mg to about 20 mg, in a unit formulation (i.e., unit dosage form). The salt of rosuvastatin may be a conventional pharmaceutically acceptable salt, such as calcium salt, hydrochloride, hydrobromide, sulfate, phosphate, acetate, maleate, fumarate, lactate, tartrate, citrate, gluconate, besylate, and camsylate. Preferably, rosuvastatin calcium may be used in the present disclosure. The pharmaceutical composition may be administered once a day, but not limited thereto.

The pharmaceutical composition has a combination dosage form having separate compartments (i.e., a double-layered tablet form), comprising or consisting essentially of a layer comprising rosuvastatin or its salt and a layer comprising olmesartan medoxomil.

When the compartment comprising rosuvastatin or its salt includes a certain disintegrant (i.e., cellulose-type and/or povidone-type disintegrants), in a certain amount, rapid disintegration and high initial dissolution rate of rosuvastatin or its salt can be accomplished, thereby being able to obtain a combination formulation bioequivalent to the single formulation of rosuvastatin or its salt. The disintegrant may be one or more selected from the group consisting of povidone (for example, Kolidone™), crospovidone (for example, Polyplasdone™), low substituted hydroxypropyl cellulose, croscarmellose sodium, and carboxymethylcellulose calcium. Preferably, the disintegrant may be a mixture of crospovidone and croscarmellose sodium; or croscarmellose sodium. The disintegrant may be present in an amount ranging from 2 to 20% by weight, preferably from 3 to 15% by weight, based on the total weight of the compartment comprising rosuvastatin or its salt. When other disintegrants are used, the dissolution rate of rosuvastatin or its salt is decreased; and/or the amount used is increased, which may cause insufficient compression force during the compressing step, thereby leading to high friability of the resulting formulation (e.g., tablet). In addition, the use of other disintegrants brings about insufficient hardness, which may cause unwanted problems in packaging or delivery.

For olmesartan medoxomil, a combination formulation comprising rosuvastatin and olmesartan medoxomil should be designed so as to exhibit high dissolution rate of olmesartan medoxomil in an in vitro comparative dissolution test, in order to obtain a bioequivalent formulation to the single formulation containing olmesartan medoxomil. In order to obtain the high in vitro dissolution rate, the compartment comprising olmesartan medoxomil comprises a preferred disintegrant, which may be one or more selected from the group consisting of low substituted hydroxypropyl cellulose, carboxymethylcellulose calcium, croscarmellose sodium, crospovidone, sodium starch glycolate, and pregelatinized starch. In an embodiment, the compartment comprising olmesartan medoxomil comprises 7.5 or more % by weight of low substituted hydroxypropyl cellulose, 5 or more % by weight of carboxymethylcellulose calcium, 15 or more % by weight of croscarmellose sodium, 10 or more % by weight of crospovidone, 5 or more % by weight of sodium starch glycolate, or 5 or more % by weight of pregelatinized starch, based on the total weight of the compartment comprising olmesartan medoxomil. In another embodiment, the compartment comprising olmesartan medoxomil comprises 7.5 to 65% by weight of low substituted hydroxypropyl cellulose, 5 to 60% by weight of carboxymethylcellulose calcium, 15 to 30% by weight of croscarmellose sodium, 10 to 40% by weight of crospovidone, 5 to 40% by weight of sodium starch glycolate, or 5 to 60% by weight of pregelatinized starch, based on the total weight of the compartment comprising olmesartan medoxomil. In a further embodiment, the compartment comprising olmesartan medoxomil comprises 7.5 to 65% by weight, preferably 10 to 60% by weight, more preferably about 20±1% by weight of low substituted hydroxypropyl cellulose, based on the total weight of the compartment comprising olmesartan medoxomil.

The pharmaceutical composition may further comprise one or more excipients conventionally used in the field of pharmaceutics, for example a diluent (or additive), a binder, a lubricant, in addition to said disintegrant. The pharmaceutical composition may be also coated with an appropriate coating agent, such as a film-coating agent.

The diluent (or additive) includes lactose (including its hydrate), dextrin, mannitol, sorbitol, starch, microcrystalline cellulose (for example, Celphere™), silicified microcrystalline cellulose (for example, Prosolv™), calcium hydrogen phosphate (including its hydrate), anhydrous calcium hydrogen phosphate, calcium carbonate, saccharides, and a mixture thereof. The binder includes polyvinylpyrrolidone, copovidone, gelatin, starch, sucrose, methyl cellulose, ethyl cellulose, hydroxyethyl cellulose, hydroxypropyl cellulose, hydroxypropyl alkylcellulose (for example, hydroxypropyl methylcellulose), and a mixture thereof. The lubricant includes stearic acid, stearates (for example, magnesium stearate), talc, corn starch, carnauba wax, light anhydrous silicic acid, magnesium silicate, synthetic aluminum silicate, hydrogenated oil, hydrogenated oil, titanium oxide, microcrystalline cellulose, macrogol 4000 or 6000, isopropyl myristate, calcium hydrogen phosphate, and a mixture thereof. The coating agent, for example a film-coating agent, includes a conventional polymer such as Opadry™. The film-coating agent may be used in a minimum amount for providing an appropriate size of the formulation, but not limited thereto.

The pharmaceutical composition having a double-layered tablet form may be prepared by preparing granules containing rosuvastatin and granules containing olmesartan medoxomil, respectively; and then compressing the mixture thereof with a double-layer tablet-press machine. If necessary, the resulting double-layered tablet may be coated with a film-coating agent such as Opadry™. The granules containing rosuvastatin and the granules containing olmesartan medoxomil may be prepared according to dry granulation methods or wet granulation methods. For example, the granules containing rosuvastatin may be prepared according to a dry granulation method. That is, the granules containing rosuvastatin may be prepared by mixing rosuvastatin calcium, an additive (diluent), a disintegrant, and a lubricant according to a conventional method; and then granulating the mixture with, e.g., a roller compactor (TF mini, Vector). Also, the granules containing olmesartan medoxomil may be prepared according to a wet granulation method. That is, the granules containing olmesartan medoxomil may be prepared by mixing olmesartan medoxomil, a binder, an additive (diluent), a disintegrant; granulating the mixture with a high speed mixer (MIC Developer-5, COMASA); and then drying and sieving the resulting granules.

Representative double-layer tablets can be prepared as described below.

Step 1. Preparation of Granules containing Rosuvastatin.

Rosuvastatin calcium, lactose monohydrate, Prosolv™, dibasic calcium phosphate dihydrate, crospovidone, croscarmellose sodium, light anhydrous silicic acid, and magnesium stearate (85% of the total amount used in the rosuvastatin-layer) were sieved through a 24 mesh and then mixed. The resulting mixture was granulated using a roller compactor (TF mini, Vector). The obtained granules were sieved through a 24 mesh and then mixed with magnesium stearate pre-sieved though a 35 mesh (15% of the total amount used in the rosuvastatin-layer) to prepare a rosuvastatin-containing granule mixture.

Step 2. Preparation of Granules containing Olmesartan Medoxomil.

Olmesartan medoxomil, hydroxypropyl cellulose, lactose monohydrate, microcrystalline cellulose, and low substituted hydroxypropyl cellulose were sieved through a 24 mesh and then mixed. The resulting mixture was granulated using a high speed mixer (MIC Developer-5, COMASA). The resulting dry granules were sieved through a 24 mesh and then mixed with magnesium stearate pre-sieved though a 35 mesh and yellow iron oxide pre-sieved through a 80 mesh to prepare a olmesartan medoxomil-containing granule mixture.

Step 3. Preparation of Double-Layered Tablets.

The rosuvastatin-containing granule mixture prepared in Step 1 and the olmesartan medoxomil-containing granule mixture prepared in Step 2 were compressed with a double-layer tablet-press machine (BB-11, RIVA) to obtain double-layered tablets. The resulting tablets were film-coated with Opadry™ in a pan coating machine (LDCS, VECTOR).

Unless specifically defined herein, all terms used herein have the same meaning as they would to one skilled in the art of the present invention. Practitioners are particularly directed to Sambrook J., et al. (eds.) *Molecular Cloning: A Laboratory Manual*, 3rd ed., Cold Spring Harbor Press, Plainsview, N.Y. (2001); Ausubel, F. M., et al. (eds.), *Current Protocols in Molecular Biology*, John Wiley & Sons, New York (2010); and Coligan, J. E., et al. (eds.), *Current Protocols in Immunology*, John Wiley & Sons, New York (2010) for definitions and terms of art.

The use of the term "or" in the claims is used to mean "and/or" unless explicitly indicated to refer to alternatives only or the alternatives are mutually exclusive, although the disclosure supports a definition that refers to only alternatives and "and/or."

Following long-standing patent law, the words "a" and "an," when used in conjunction with the word "comprising" in the claims or specification, denotes one or more, unless specifically noted.

Unless the context clearly requires otherwise, throughout the description and the claims, the words "comprise," "comprising," and the like, are to be construed in an inclusive sense as opposed to an exclusive or exhaustive sense; that is to indicate, in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application. Unless stated otherwise, the term "about" implies minor variation around the stated value of no more than 10% (above or below).

Disclosed are materials, compositions, and devices that can be used for, can be used in conjunction with, can be used in preparation for, or are products of the disclosed methods and compositions. It is understood that, when combinations, subsets, interactions, groups, etc., of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

Publications cited herein and the subject matter for which they are cited are hereby specifically incorporated by reference in their entireties.

The following examples are provided for the purpose of illustrating, not limiting, the disclosure.

EXAMPLES

Example 1

Olmsartan Antibodies

Antibodies against olmesartan were sought using a goat polyclonal approach and a mouse monoclonal approach.

Polyclonal Antibodies

Figure 3:
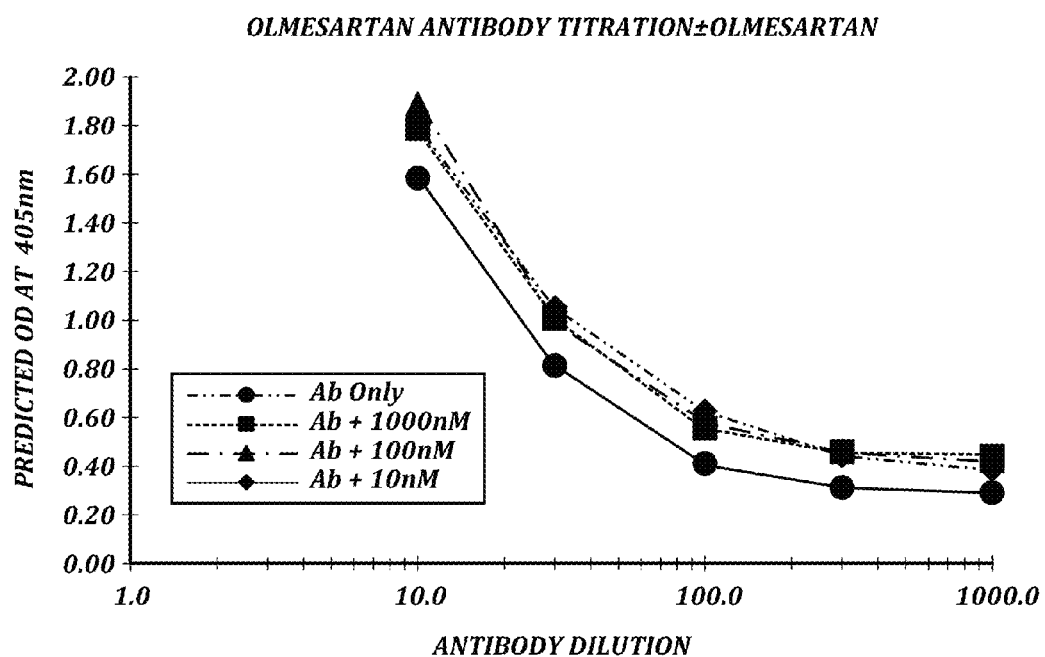
FIG. 3 is a graph comparing the antibody dilution in competitive ELISA detection of olmesartan in solution using polyclonal antisera against olmesartan and immobilized olmesartan-protein conjugate. The serum from the production bleed was evaluated for titration (Ab Only) and against olmesartan at three concentrations (Ab+1000 nM olmesartan, Ab+100 nM olmesartan, Ab+10 nM olmesartan). Titration in the presence of olmesartan at any concentration demonstrates a lack of antibody specificity in the serum sample.

Goats were immunized with a KLH-olmesartan conjugate. Despite repeated immunization, it was not possible to raise effective polyclonal antisera against olmesartan. To illustrate, FIG. 3 shows the results of a competitive ELISA using the anti-sera were applied in a competitive format at various dilutions using immobilized olmesartan-protein conjugate. The negative result for seeking to raise a polyclonal against olmesartan relates to the difficulty in overall development of a monoclonal antibody against olmesartan.

Monoclonal Antibodies

Figure 4:
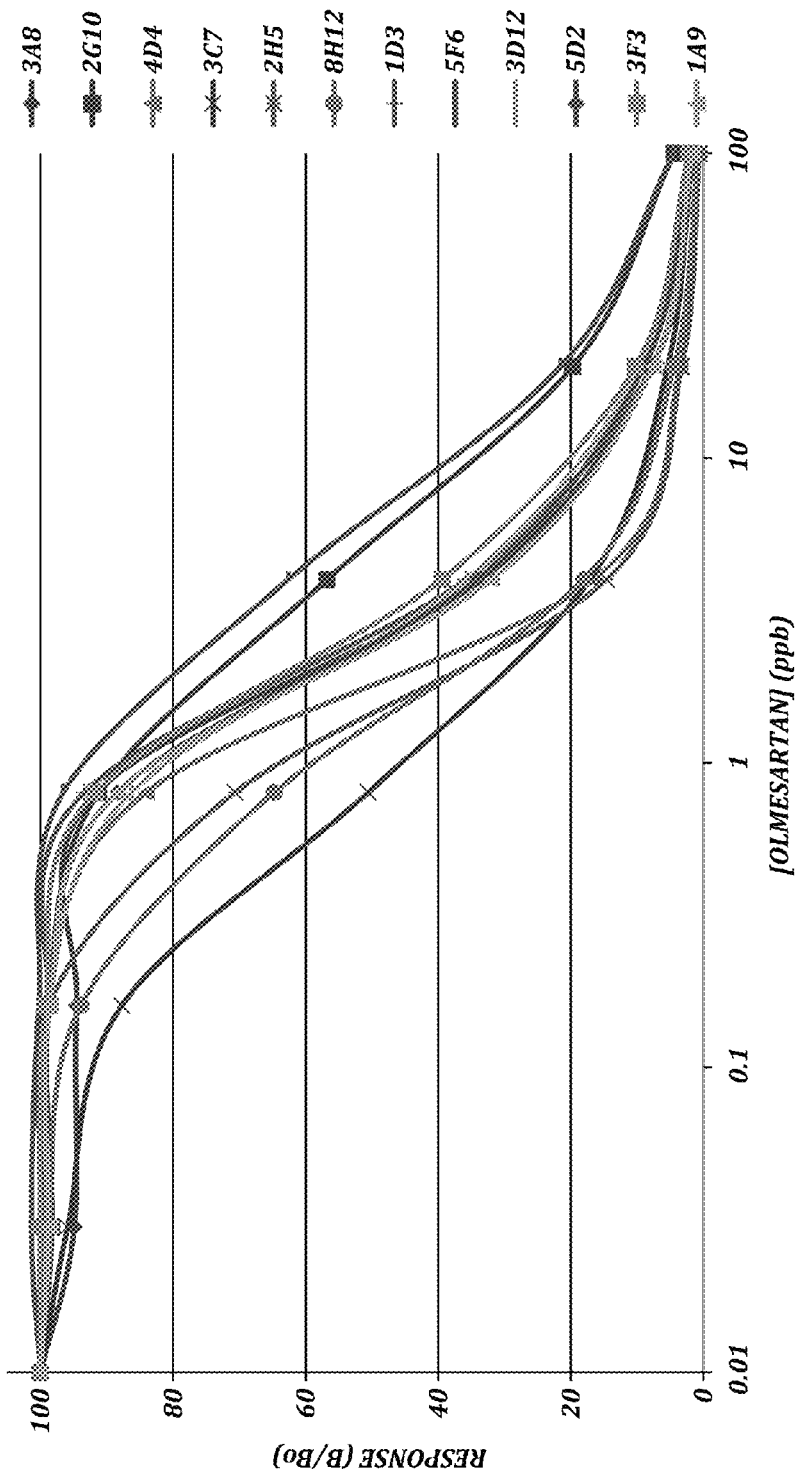
FIG. 4 is a graph comparing the effectiveness of anti-olmesartan monoclonal antibody clones having varying affinities in competitive ELISA detection of olmesartan in solution using an immobilized olmesartan-bovine serum albumin (BSA) conjugate.

A bovine serum albumin (BSA)-olmesartan conjugate was generated using olmesartan acid as a starting template. The carboxylic acid was reacted with the amino group on BSA to create an amide bond between BSA and olmesartan. To produce monoclonal antibodies, ten mice were immunized with BSA-olmesartan conjugate under a standard immunization cycle. When the antibody titer was determined for each individual to be sufficiently high, the spleen was removed and B cells were isolated and fused with myeloma cells accordingly to accepted protocols. The fused hybridoma cells were screened using BSA-olmesartan and BSA (for negative screen) to identify anti-omesartan mAb. Results of competitive ELISA assays for generated monoclonal antibodies using immobilized olmesartan-protein conjugate or BSA-olmesartan conjugate are shown in FIGS. 4 and 5, respectively. The successful hybridoma cell lines were expanded for expression and purification of the anti-omesartan mAb.

Example 2

Assay Reagents

In this example, the preparation of representative reagents, e.g., detection and capture reagents, useful in the representative immune-assay methods and devices of the disclosure are described.

Detection Reagents: Antibody-Colloidal Gold Conjugates.

Briefly, 1) colloidal gold solution was adjusted to desired pH; 2) specific antibody was then added to the colloidal gold solution to reach specific concentration of either 8 ug/ml or 10 ug/ml and allowed to react for approximately 10 minutes at room temperature; 3) the reaction was stopped by adding sufficient volume of 10% BSA solution to yield a final 1% BSA concentration; 4) the conjugate solution was centrifuged at 16,000 g at rm temp for 10 minutes; 5) the supernatant was carefully aspirated off and the pellet re-suspend in diluent buffer to reach desired OD concentration.

Capture Reagents: Drug-Albumin Conjugates.

Drug-albumin conjugates (e.g., BSA-olmesartan) were prepared as described above.

In one exemplary embodiment, a lateral flow system was evaluated. A 1.0 mg/mL BSA-olmesartan (Test line) and 0.2 mg/mL goat anti-mouse antibody (Control line) were striped onto the system's membrane. Olmesartan antibody-colloidal gold conjugate was flowed through the system. The anti-body-colloidal gold conjugate bound to BSA-olmesartan immobilized on the membrane and generated a strong signal. The signal was specific to olmesartan because a decreased signal was observed when olmesartan was spiked into the samples.

Example 3

Representative Solid Phase Competitive Assay

In this example, a representative assay demonstrating the efficacy of a solid-phase competitive assay is described. The assay demonstrates the utility of using a representative antibody (anti-olmesartan antibodies described herein) in such a detection format to provide informative signals for the presence and amount of olmesartan in a sample.

Lateral Flow System.

Two versions of the lateral flow format were used. The first incorporated a single test line (T) as illustrated in FIG. 2C, and the second incorporated two test lines (T1 and T2) as illustrated in FIG. 2D. The test lines of BSA-olmesartan (T, or T1 and T2) and a control line (C) of goat-anti-mouse antibody were striped onto a membrane card (high-flow plus HF180 membrane card, Millipore). The test lines T (or T1) were striped with 1.0 mg/mL BSA-olmesartan and, when tested, the additional test line T2 was striped with 0.5 mg/ml BSA-olmesartan. 0.2 mg/ml of goat-anti-mouse antibody was striped for the control (C) line.

Ruby-color colloidal gold was used to provide a signal on the agent and was made from gold(III) chloride and the pH of gold solution was adjusted to a range of pH 6.0 to pH 9.5. The specific anti-olmesartan antibody being tested was conjugated to the colloidal gold through passive absorption.

The solution of antibody-gold conjugate was directly applied to the conjugated pad while running the assay (i.e., a "liquid phase" assay). 5, 6 or 7 ul mAb-gold conjugate (OD10) was mixed with 10 ul of sample containing different amounts of olmesartan. The mixture was applied to the conjugate pad (glass fiber pad, Millipore) of the strip and chased with 80-90 ul of chasing buffer. Assay time is 15-20 mins before taking the reading.

A "solid phase" lateral flow assay can be performed by applying and drying the detection reagent (e.g., anti-olmesartan antibody conjugated with gold colloid) to the conjugate pad. For example, 8% (w/v) sucrose and 2% (w/v) trehalose are used to stabilize mAb-gold conjugate when drying onto the conjugate pad. 10 ul of sample containing different amount of olmesartan is applied to the test trip and chased with 80-90 ul of chasing buffer. Assay time is 15-20 mins before taking the reading.

Reader Output: Intensity vs Position.

Readout of the results of scanning the test strips was generated using Qiagen reader (Qiagen, Germany). The intensity (peak area) of the test line(s) and control line is measured and the ratio of Testline/Control (T/C) line was calculated.

Standard Curve.

Standard curves of ratio of Testline/Control (T/C) vs. olmesartan concentration were generated in the "liquid phase" format and are illustrated in FIGS. 5A-10.

Figure 5A:
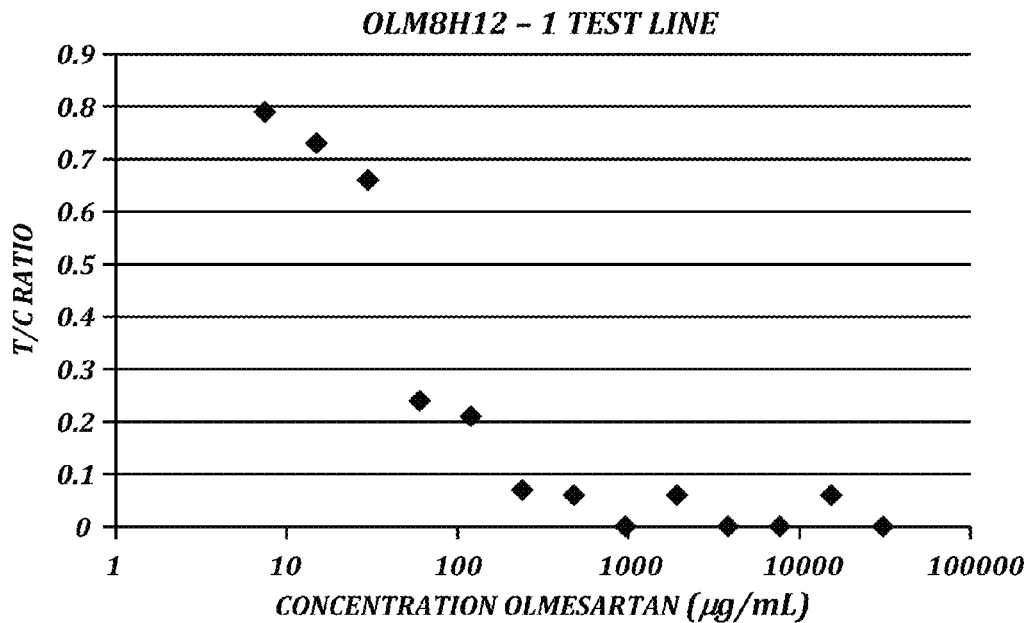
FIGS. 5A and 5B illustrate curves for a first representative anti-olmesartan monoclonal antibody (OLM8H12) bound in a representative lateral flow assay with one test line (FIG. 5A) or two test lines (FIG. 5B) carried out with a device of the disclosure using the representative test strips illustrated in FIGS. 2C and 2D, respectively. The illustrated standard curves show the ratio of test line over control line (T/C) vs. drug concentration.
Figure 5B:
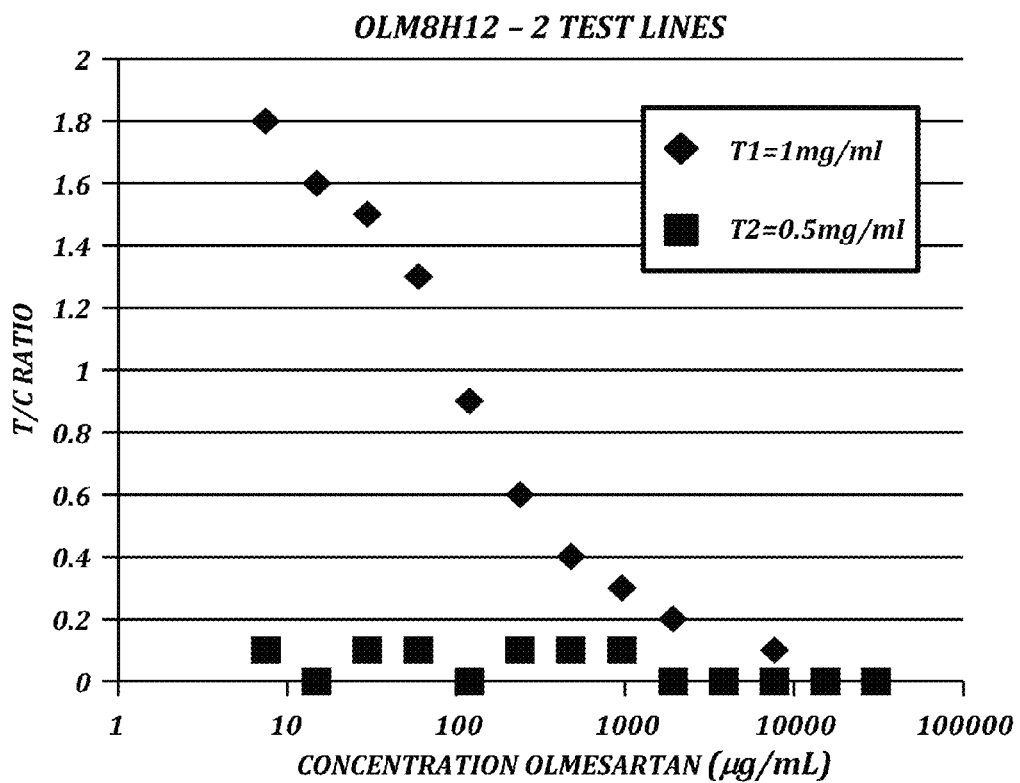

FIG. 5A illustrates the standard curve, i.e., the ratio of test line over control line (T/C) vs. olmesartan concentration for the lateral flow assay (LFA) using the anti-olmesartan monoclonal antibody OLM8H12. In this assay, a single test (T) line of BSA-olmesartan was striped at 1 mg/ml. 5 µl of 8 µg/ml OLM8H12 mAb/colloidal gold conjugate (pH 7.0; OD10) was applied onto the conjugate pad. FIG. 5B illustrates the standard curves for an LFA using two test lines (T1 and T2) of the anti-olmesartan monoclonal antibody OLM8H12. T1 was striped at 1 mg/ml BSA-olmesartan and T2 was striped at 0.5 mg/ml BSA-olmesartan. 5 µl of 8 µg/ml OLM8H12 mAb/colloidal gold conjugate (pH 6.5; OD10) was applied onto the conjugate pad. Both assays illustrate that the anti-olmesartan monoclonal antibody OLM8H12 exhibited high sensitivity for olmesartan with detectable binding at the T (or T1) line reduced only at higher concentrations of competing olmesartan spiked into the flow. The large difference in T/C ratio between the T1 and T2 lines observed in the two line test (FIG. 5B) demonstrates a much higher sensitivity for the antibody when placed closer to the sample port, where concentration of analyte is likely to be higher.

Figure 6A:
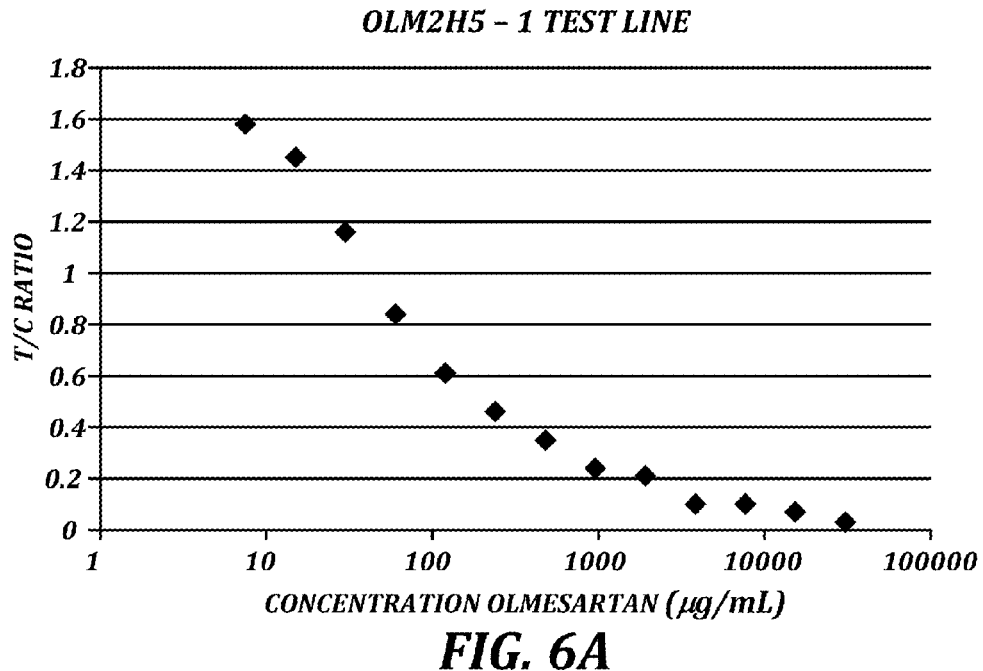
FIGS. 6A and 6B illustrate curves for another representative anti-olmesartan monoclonal antibody (OLM2H5) bound in a representative lateral flow assay with one test line (FIG. 6A) or two test lines (FIG. 6B) carried out with a device of the disclosure using the representative test strip illustrated in FIGS. 2C and 2D, respectively. The illustrated standard curves show the ratio of test line over control line (T/C) vs. drug concentration.
Figure 6B:
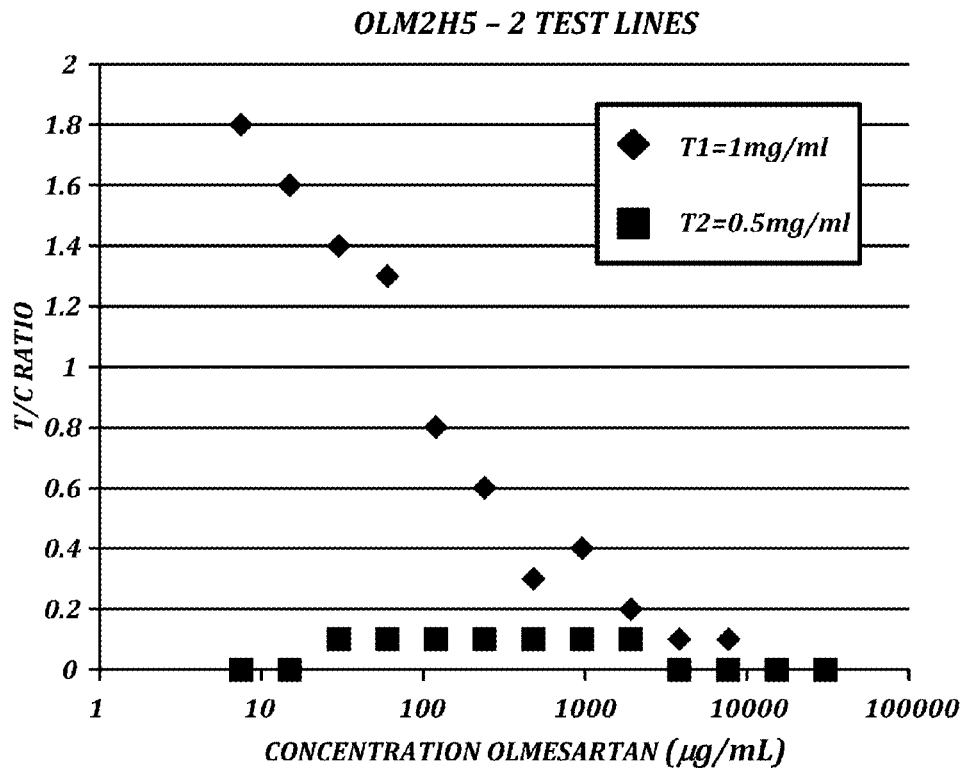

FIG. 6A illustrates the standard curve, i.e., the ratio of test line over control line (T/C) vs. olmesartan concentration for the LFA using the anti-olmesartan monoclonal antibody OLM2H5. In this assay, a single test (T) line of BSA-olmesartan was striped at 1 mg/ml. 7 µl of 8 µg/ml OLM2H5 mAb/colloidal gold conjugate (pH 7.0; OD10) was applied onto the conjugate pad. FIG. 6B illustrates the standard curves for an LFA using two test lines (T1 and T2) of the anti-olmesartan monoclonal antibody OLM2H5. T1 was striped at 1 mg/ml BSA-olmesartan and T2 was striped at 0.5 mg/ml BSA-olmesartan. 5 µl of 8 µg/ml OLM2H5 mAb/colloidal gold conjugate (pH 7.0; OD10) was applied onto the conjugate pad. Both assays illustrate that the anti-olmesartan monoclonal antibody OLM2H5 exhibited high sensitivity for olmesartan with detectable binding at the T (or T1) line reduced only at higher concentrations of competing olmesartan spiked into the flow. The large difference in T/C ratio between the T1 and T2 lines observed in the two line test (FIG. 6B) demonstrates a much higher sensitivity for the antibody when placed closer to the sample port, where concentration of analyte is likely to be higher.

Figure 7A:
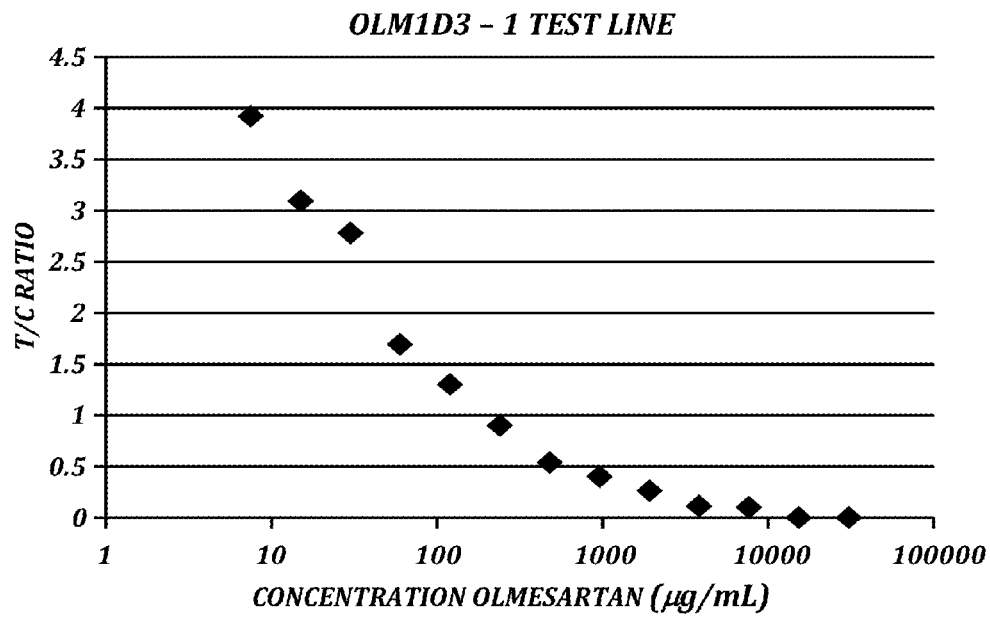
FIGS. 7A and 7B illustrate curves for another representative anti-olmesartan monoclonal antibody (OLM1D3) bound in a representative lateral flow assay with one test line (FIG. 7A) or two test lines (FIG. 7B) carried out with a device of the disclosure using the representative test strip illustrated in FIGS. 2C and 2D, respectively. The illustrated standard curves show the ratio of test line over control line (T/C) vs. drug concentration.
Figure 7B:
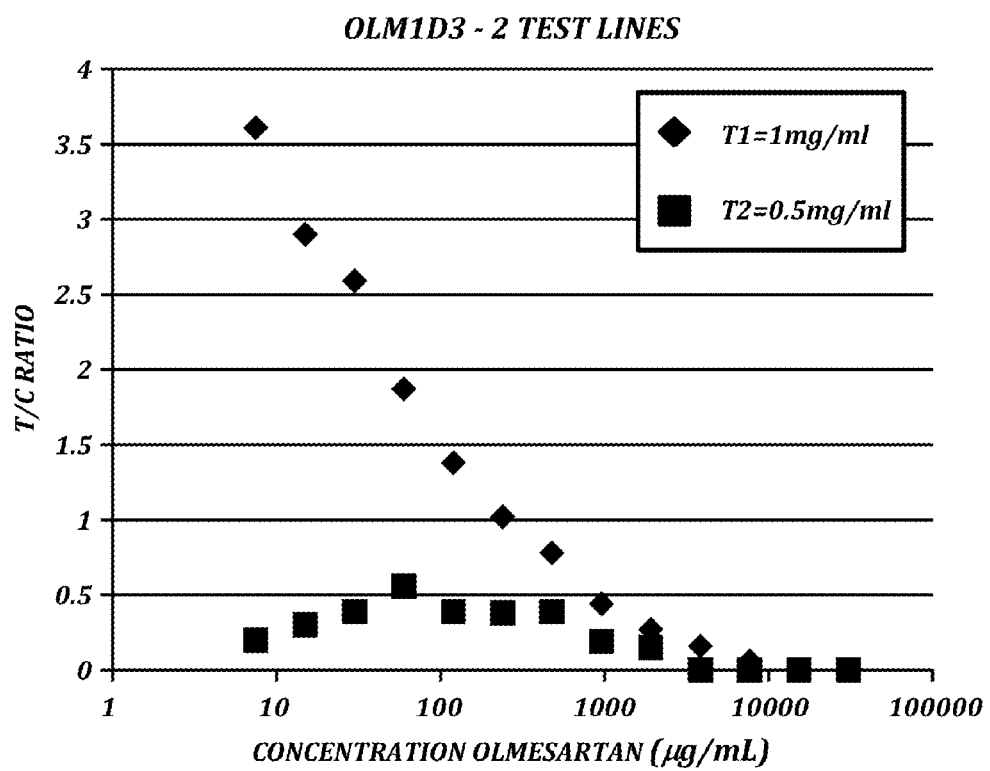

FIG. 7A illustrates the standard curve, i.e., the ratio of test line over control line (T/C) vs. olmesartan concentration for the LFA using the anti-olmesartan monoclonal antibody OLM1D3. In this assay, a single test (T) line of BSA-olmesartan was striped at 1 mg/ml. 5 µl of 10 µg/ml OLM1D3 mAb/colloidal gold conjugate (pH 8.0; OD10) was applied onto the conjugate pad. FIG. 7B illustrates the standard curves for an LFA using two test lines (T1 and T2) of the anti-olmesartan monoclonal antibody OLM1D3. T1 was striped at 1 mg/ml BSA-olmesartan and T2 was striped at 0.5 mg/ml BSA-olmesartan. 5 µl of 10 µg/ml OLM1D3 mAb/colloidal gold conjugate (pH 8.0; OD10) was applied onto the conjugate pad. Both assays illustrate that the anti-olmesartan monoclonal antibody OLM1D3 exhibited high sensitivity for olmesartan with detectable binding at the T (or T1) line reduced only at higher concentrations of competing olmesartan spiked into the flow. The large difference in T/C ratio between the T1 and T2 lines observed in the two line test (FIG. 7B) demonstrates a much higher sensitivity for the antibody when placed closer to the sample port, where concentration of analyte is likely to be higher.

Figure 8A:
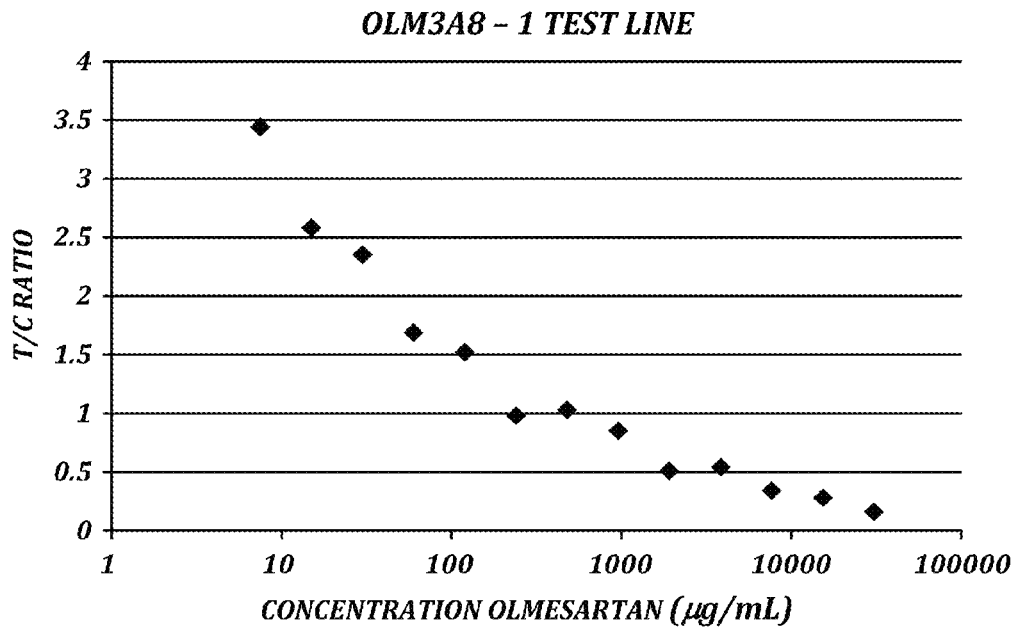
FIGS. 8A and 8B illustrate curves for another representative anti-olmesartan monoclonal antibody (OLM3A8) bound in a representative lateral flow assay with one test line (FIG. 8A) or two test lines (FIG. 8B) carried out with a device of the disclosure using the representative test strip illustrated in FIGS. 2C and 2D, respectively. The illustrated standard curves show the ratio of test line over control line (T/C) vs. drug concentration.
Figure 8B:
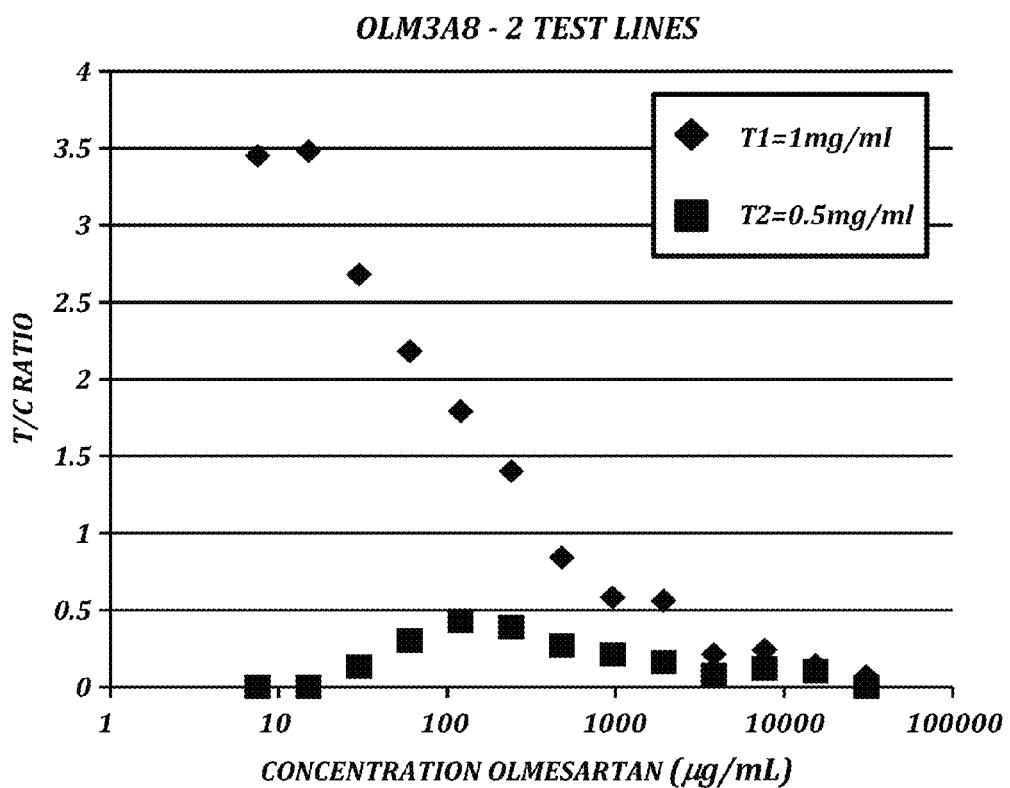

FIG. 8A illustrates the standard curve, i.e., the ratio of test line over control line (T/C) vs. olmesartan concentration for the LFA using the anti-olmesartan monoclonal antibody OLM3A8. In this assay, a single test (T) line of BSA-olmesartan was striped at 1 mg/ml. 6 μl of 10 μg/ml OLM3A8 mAb/colloidal gold conjugate (pH 8.0; OD10) was applied onto the conjugate pad. FIG. 8B illustrates the standard curves for an LFA using two test lines (T1 and T2) of the anti-olmesartan monoclonal antibody OLM3A8. T1 was striped at 1 mg/ml BSA-olmesartan and T2 was striped at 0.5 mg/ml BSA-olmesartan. 6 μl of 10 μg/ml OLM3A8 mAb/colloidal gold conjugate (pH 8.0; OD10) was applied onto the conjugate pad. Both assays illustrate that the anti-olmesartan monoclonal antibody OLM3A8 exhibited high sensitivity for olmesartan with detectable binding at the T (or T1) line reduced only at higher concentrations of competing olmesartan spiked into the flow. The large difference in T/C ratio between the T1 and T2 lines observed in the two line test (FIG. 8B) demonstrates a much higher sensitivity for the antibody when placed closer to the sample port, where concentration of analyte is likely to be higher.

Figure 9A:
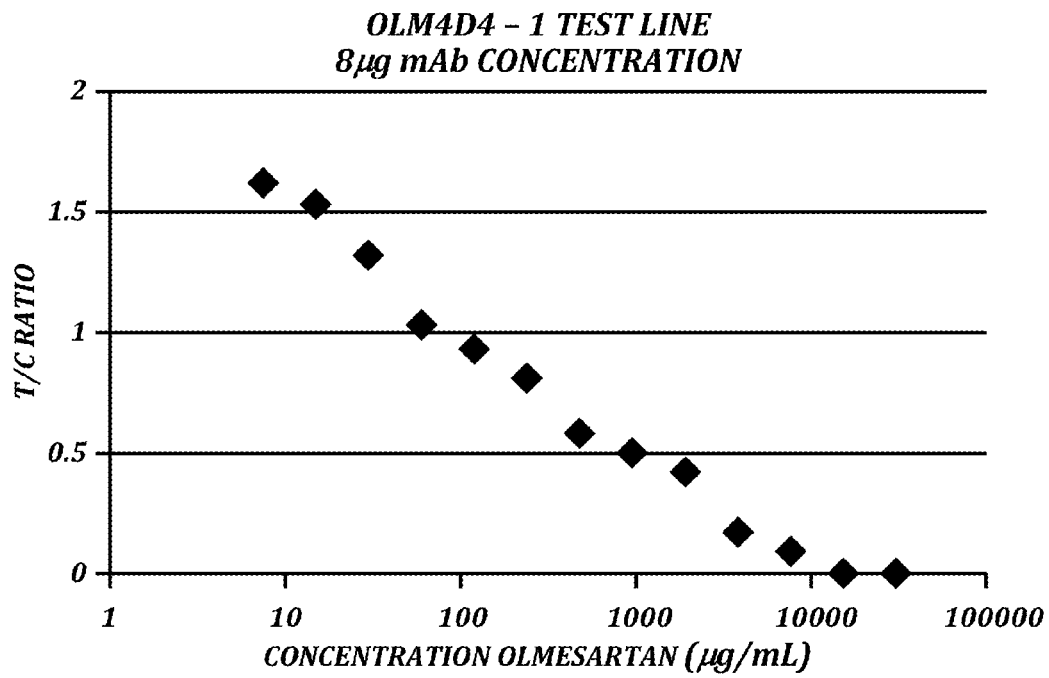
FIGS. 9A-9D illustrate curves for another representative anti-olmesartan monoclonal antibody (OLM4D4) bound in a representative lateral flow assay with different concentrations of antibody using one test line (FIGS. 9A and 9B) or two test lines (FIGS. 9C and 9D) and carried out with a device of the disclosure using the representative test strip illustrated in FIGS. 2C and 2D, respectively. The illustrated standard curves show the ratio of test line over control line (T/C) vs. drug concentration.
Figure 9B:
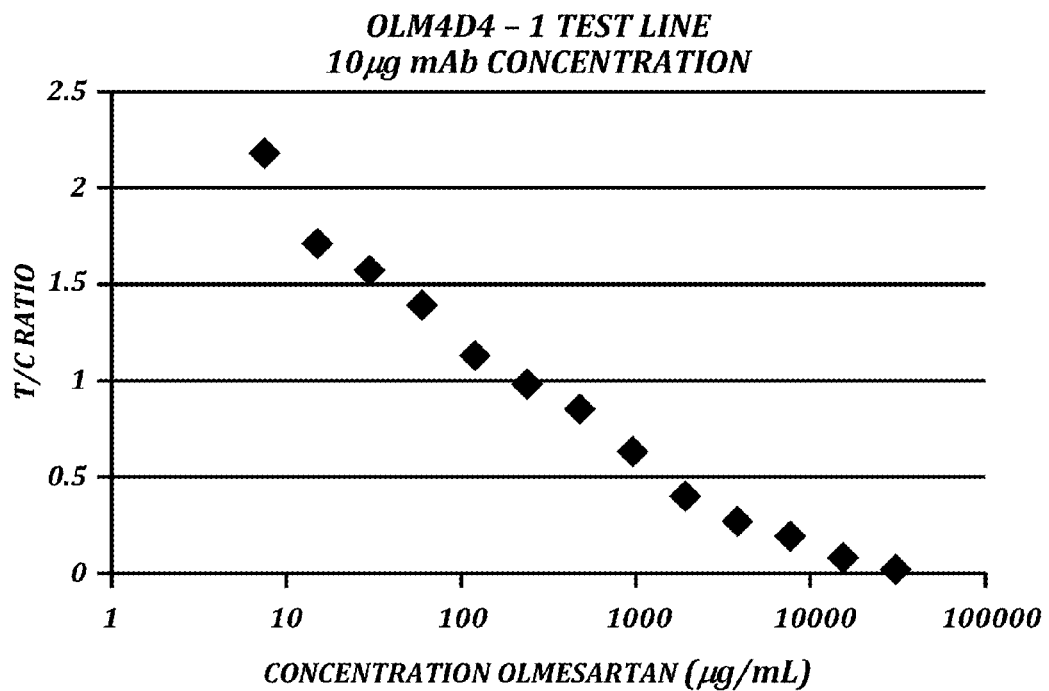
Figure 9C:
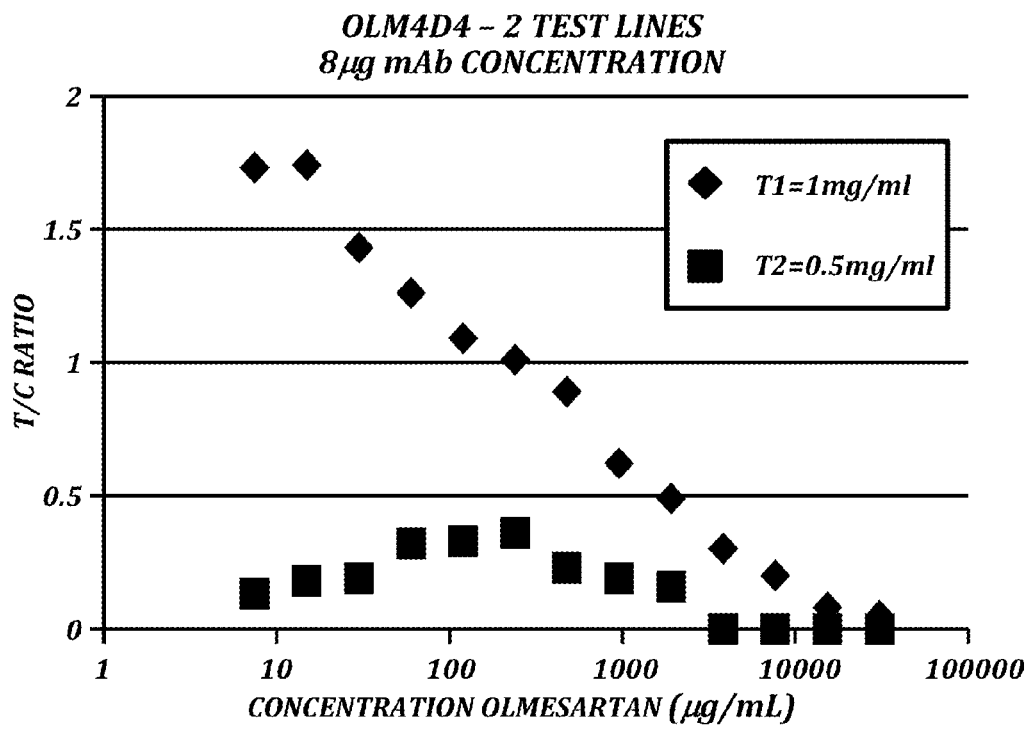
Figure 9D:
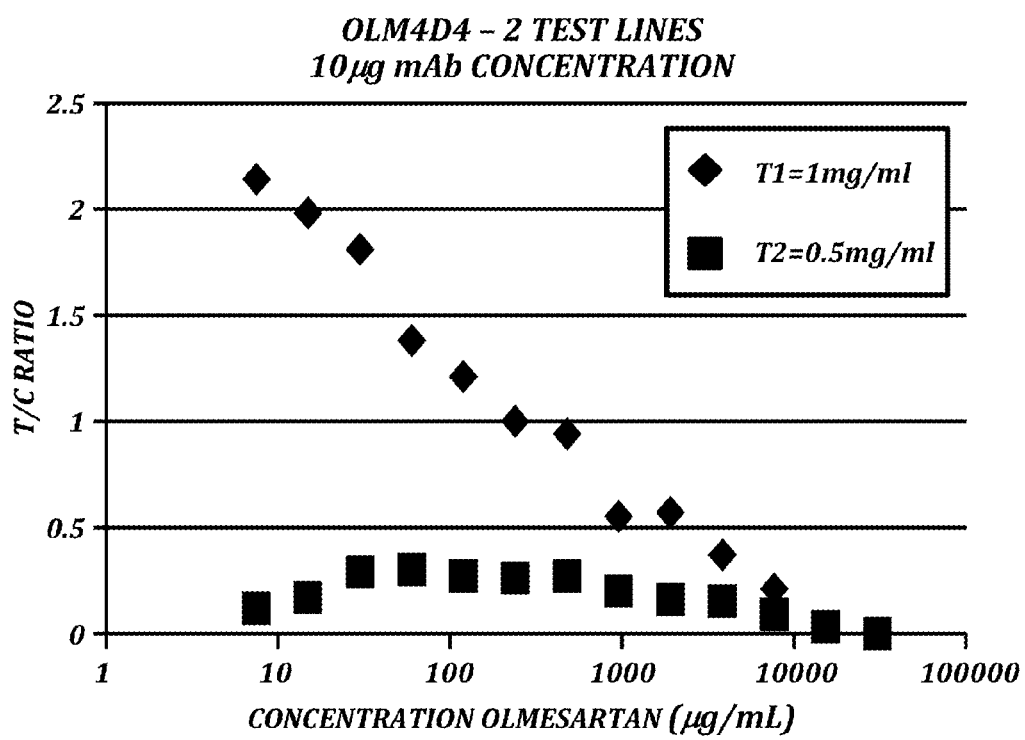

FIGS. 9A and 9B illustrate the standard curves, i.e., the ratio of test line over control line (T/C) vs. olmesartan concentration for two LFAs using the anti-olmesartan monoclonal antibody OLM4D4. In these assays, a single test (T) line of BSA-olmesartan was striped at 1 mg/ml. 5 μl of 8 μg/ml (FIG. 9A) or 10 μg/ml (FIG. 9B) OLM4D4 mAb/colloidal gold conjugate (pH 8.0; OD10) was applied onto the conjugate pad. FIGS. 9C and 9D illustrate the standard curves for LFAs using two test lines (T1 and T2) of the anti-olmesartan monoclonal antibody OLM4D4. T1 was striped at 1 mg/ml BSA-olmesartan and T2 was striped at 0.5 mg/ml BSA-olmesartan. For each LFA, 5 μl of 8 μg/ml (FIG. 9C) or 10 μg/ml (FIG. 9D) OLM4D4 mAb/colloidal gold conjugate (pH 8.0; OD10) was applied onto the conjugate pad. All of the assays illustrate that the anti-olmesartan monoclonal antibody OLM4D4 exhibited high sensitivity for olmesartan with detectable binding at the T (or T1) line reduced only at higher concentrations of competing olmesartan spiked into the flow. The large differences in T/C ratios between the T1 and T2 lines observed in the two line tests (FIGS. 9C and 9D) demonstrate a much higher sensitivity for the antibody when placed closer to the sample port, where concentration of analyte is likely to be higher.

Figure 10:
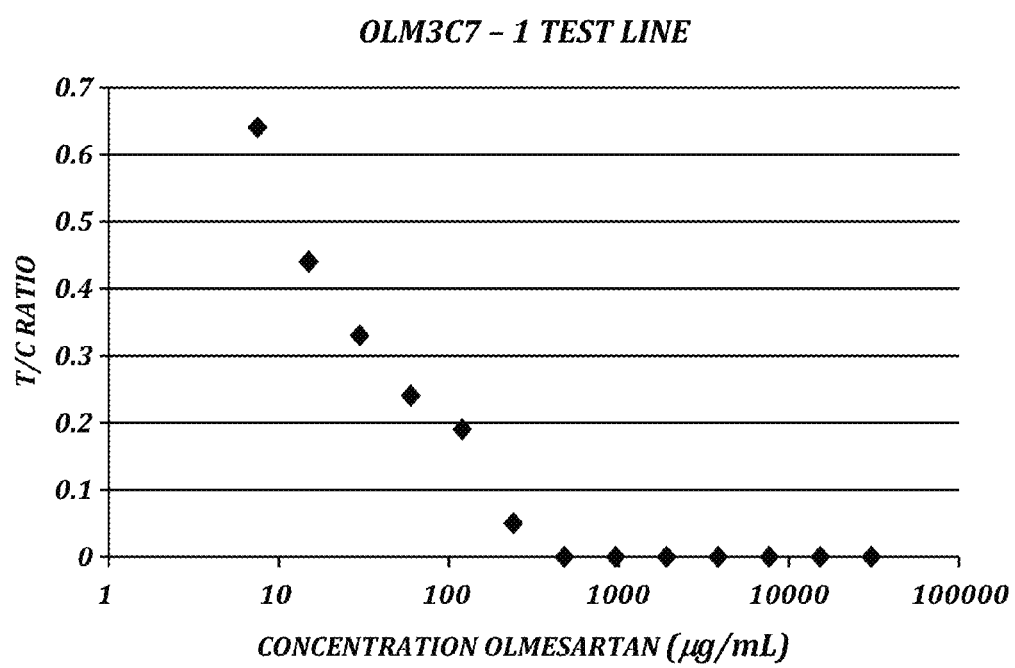
FIG. 10 illustrates a curve for another representative anti-olmesartan monoclonal antibody (OLM3C7) bound in a representative lateral flow assay with one test line carried out with a device of the disclosure using the representative test strip illustrated in FIG. 2C. The illustrated standard curve shows the ratio of test line over control line (T/C) vs. drug concentration.

FIG. 10 illustrates the standard curve, i.e., the ratio of test line over control line (T/C) vs. olmesartan concentration for an LFA using the anti-olmesartan monoclonal antibody OLM3C7. In this assay, a single test (T) line of BSA-olmesartan was striped at 1 mg/ml. 5 μl of 8 μg/ml OLM3C7 mAb/colloidal gold conjugate (pH 7.5; OD10) was applied onto the conjugate pad. The anti-olmesartan monoclonal antibody OLM3C7 exhibited high sensitivity for olmesartan with detectable binding at the T line reduced only at higher concentrations of competing olmesartan spiked into the flow.

While illustrative embodiments have been illustrated and described, it will be appreciated that various changes can be made therein without departing from the spirit and scope of the disclosure.

The embodiments of the invention in which an exclusive property or privilege is claimed are defined as follows:

1. A method of detecting the presence of olmesartan in a sample, comprising:
    contacting the sample to an anti-olmesartan antibody or antigen-binding fragment or derivative thereof labeled with a detectable reporting group under conditions sufficient to permit binding of olmesartan in the sample with the antibody or antigen-binding fragment or derivative thereof, wherein the anti-olmesartan antibody is a monoclonal antibody and the antibody or antigen-binding fragment or derivative thereof has a 50% binding of immobilized olmesartan at between 2.0 and 5.0 ppb free olmesartan in a competitive ELISA; and
    detecting the binding of the olmesartan to the antibody or antigen-binding fragment or derivative thereof, wherein the detecting the presence of olmesartan in the sample is performed in a lateral flow assay format.

2. The method of claim 1, wherein the lateral flow assay format comprises:
    (a) applying a liquid sample comprising olmesartan to a lateral flow assay device, the device comprising:
        (i) a sample receiving zone for receiving the liquid sample;
        (ii) a detection reagent zone in liquid communication with the sample receiving zone and downstream in flow direction from the sample receiving zone, wherein the detection reagent zone comprises a detection reagent deposited thereon, and wherein the detection reagent comprises the anti-olmesartan antibody or antigen-binding fragment or derivative thereof labeled with a detectable reporting group; and
        (iii) a capture zone in liquid communication with the detection reagent zone and downstream in flow direction from the detection reagent zone, wherein the capture zone comprises a first capture reagent immobilized thereon, wherein the first capture reagent comprises an olmesartan structure capable of binding the detection reagent; and
    (b) allowing the sample to flow from the sample receiving zone through the detection reagent zone to provide a detection reagent with olmesartan;
    (c) allowing the detection reagent with olmesartan to flow through the capture zone, whereby the first capture reagent binds free detection reagent to provide detection reagent bound to the first capture reagent; and
    (d) observing the amount of detection reagent bound to the first capture reagent.

3. The method of claim 2, wherein the capture zone further comprises a second capture reagent immobilized thereon at a position downstream from the first capture reagent, wherein the second capture reagent is an antibody or antibody fragment or derivative capable of binding the detection reagent irrespective of whether the detection reagent is bound to olmesartan, and
    wherein the method comprises in step (d) observing the amount of detection reagent bound to the first capture reagent relative to the second capture reagent.

4. The method of claim 3, further comprising determining the quantity of olmesartan in the sample by quantifying the amount of detection reagent bound by the first capture reagent and the second capture reagent.

5. The method of claim 4, wherein quantifying the amount of detection reagent bound to the capture reagents comprises optical density measurement.

6. The method of claim 2, wherein the detectable reporting group is selected from colloidal gold, latex particles, colored dyes, paramagnetic particles, and fluorescent particles.

7. The method of claim 2, wherein the olmesartan structure is an olmesartan antigen that competes with olmesartan for binding to the detection reagent.

8. The method of claim 2, wherein the first capture reagent is an olmesartan-protein conjugate.

9. The method of claim 2, wherein the distance between the sample receiving zone and the first capture reagent is varied to optimize olmesartan detection sensitivity.

10. The method of claim 3, further comprising observing the amount of excess detection reagent bound to the second capture reagent.

11. The method of claim 3, further comprising determining the quantity of olmesartan in the sample by quantitating the amount of excess detection reagent bound to the second capture reagent.

12. The method of claim 1, wherein the sample is a liquid biological sample obtained from a subject, and wherein the subject was previously administered olmesartan or a prodrug thereof.

* * * * *